(12) United States Patent
Shang et al.

(10) Patent No.: US 12,072,452 B2
(45) Date of Patent: Aug. 27, 2024

(54) FLAT PANEL DETECTOR AND MANUFACTURING METHOD THEREOF

(71) Applicants: BEIJING BOE SENSOR TECHNOLOGY CO., LTD., Beijing (CN); BOE TECHNOLOGY GROUP CO., LTD., Beijing (CN)

(72) Inventors: Jianxing Shang, Beijing (CN); Xuecheng Hou, Beijing (CN); Yongsheng Zhang, Beijing (CN)

(73) Assignees: BEIJING BOE SENSOR TECHNOLOGY CO., LTD., Beijing (CN); BOE TECHNOLOGY GROUP CO., LTD., Beijing (CN)

(*) Notice: Subject to any disclaimer, the term of this patent is extended or adjusted under 35 U.S.C. 154(b) by 133 days.

(21) Appl. No.: 17/789,826

(22) PCT Filed: May 19, 2021

(86) PCT No.: PCT/CN2021/094474
§ 371 (c)(1),
(2) Date: Jun. 29, 2022

(87) PCT Pub. No.: WO2022/001440
PCT Pub. Date: Jan. 6, 2022

(65) Prior Publication Data
US 2022/0390623 A1    Dec. 8, 2022

(30) Foreign Application Priority Data
Jun. 29, 2020   (CN) .................... 202010607415.0

(51) Int. Cl.
*G01T 1/20*      (2006.01)
*G01N 23/04*     (2018.01)
*H01L 27/146*    (2006.01)

(52) U.S. Cl.
CPC ........... *G01T 1/2002* (2013.01); *G01N 23/04* (2013.01); *G01T 1/20185* (2020.05);
(Continued)

(58) Field of Classification Search
CPC ............... G01T 1/2002; G01T 1/20185; G01T 1/20187; G01N 23/04; G01N 2223/421;
(Continued)

(56) References Cited

U.S. PATENT DOCUMENTS 6,469,307 B2   10/2002  Takabayashi et al.
7,375,341 B1 *  5/2008  Nagarkar .............. G01T 1/2002
                                                    250/370.11
(Continued)

FOREIGN PATENT DOCUMENTS

CN       1152265 C       6/2004
CN     202217061 U       5/2012
(Continued)

OTHER PUBLICATIONS

Extended European Search Report from European Patent Application No. 21834609.6 dated Jan. 9, 2023.

*Primary Examiner* — Kiho Kim
(74) *Attorney, Agent, or Firm* — Dilworth & Barrese, LLP.; Michael J. Musella, Esq.

(57) ABSTRACT

Disclosed are a flat panel detector and a manufacturing method thereof. The flat panel detector including: a first optical assembly, having a first side and a second side opposite to the first side in a thickness direction of the flat panel detector, and including: a first scintillator layer configured for converting at least part of rays into a first visible light; and a first light guide component stacked with the first scintillator layer and configured for guiding the first visible light; a first image sensor assembly stacked with the first optical assembly, configured for receiving the first visible (Continued)

light, and including: a first image sensor located at the first side of the first optical assembly; and a second image sensor located at the second side of the first optical assembly.

18 Claims, 11 Drawing Sheets

(52) U.S. Cl.
CPC .. *H01L 27/14623* (2013.01); *H01L 27/14625* (2013.01); *H01L 27/14634* (2013.01); *H01L 27/14663* (2013.01); *H01L 27/14685* (2013.01); *H01L 27/1469* (2013.01); *G01N 2223/421* (2013.01); *G01N 2223/505* (2013.01)

(58) Field of Classification Search
CPC ......... G01N 2223/505; G01N 2223/03; G01N 2223/42; G01N 2223/501; H01L 27/14623; H01L 27/14625; H01L 27/14634; H01L 27/14663; H01L 27/14685; H01L 27/1469; A61B 6/42; A61B 6/4208; A61B 6/4258; Y02P 70/50; G01V 5/0016

See application file for complete search history.

(56) References Cited

U.S. PATENT DOCUMENTS

| | | |
|---|---|---|
| 9,529,097 B1 | 12/2016 | Dolinsky et al. |
| 11,237,281 B2 | 2/2022 | Zhan et al. |
| 2005/0151084 A1 | 7/2005 | Zibulevsky et al. |
| 2013/0048866 A1 | 2/2013 | Nishino et al. |
| 2019/0159749 A1* | 5/2019 | Mollov ............... G06T 5/50 |
| 2019/0361133 A1 | 11/2019 | Jin |

FOREIGN PATENT DOCUMENTS

| | | |
|---|---|---|
| CN | 202523710 U | 11/2012 |
| CN | 104538408 A | 4/2015 |
| CN | 106443754 A | 2/2017 |
| CN | 106536588 A | 3/2017 |
| CN | 109313277 A | 2/2019 |
| CN | 109545810 A | 3/2019 |
| CN | 110137199 A | 8/2019 |
| CN | 110987982 A | 4/2020 |

\* cited by examiner

Forming the first image sensor, and forming the first scintillator layer on the side of the first image sensor facing the second image sensor Attaching the first light guide component to the first scintillator layer Directly forming the second image sensor on the first light guide component

FLAT PANEL DETECTOR AND MANUFACTURING METHOD THEREOF

CROSS-REFERENCE TO RELATED APPLICATIONS

For all purposes, the present application is based on and claims the priority of Chinese patent application No. 202010607415.0 filed on Jun. 29, 2020 and titled "flat panel detector and manufacturing method thereof", and the disclosure of which is incorporated herein by its reference in its entirety as part of the present application.

TECHNICAL FIELD

At least one embodiment of the present disclosure relates to a flat panel detector and a manufacturing method of the flat panel detector.

BACKGROUND

X-ray detection technology has broad application prospects, and has been widely used in industrial nondestructive detection, container scanning, circuit board detection, medical treatment, security, industry and other fields. X-ray digital radio photography (DR) uses X-ray flat panel detectors to convert X-ray images into digital images. According to different structures, X-ray flat panel detectors are divided into direct DR and indirect DR.

SUMMARY

Accordingly to first aspect of the present disclosure, it is provided a flat panel detector comprising:
- a first optical assembly, having a first side and a second side opposite to the first side in a thickness direction of the flat panel detector, and comprising: a first scintillator layer configured for converting at least part of rays into a first visible light; and a first light guide component stacked with the first scintillator layer and configured for guiding the first visible light;
- a first image sensor assembly stacked with the first optical assembly, configured for receiving the first visible light, and comprising: a first image sensor located at the first side of the first optical assembly; and a second image sensor located at the second side of the first optical assembly.

For example, in above-mentioned flat panel detector, the first light guide component comprises a first optical fiber, and the first optical fiber is located at least on one side of the first scintillator layer in the thickness direction of the flat panel detector.

For example, in above-mentioned flat panel detector, the first optical fiber is located between the first scintillator layer and the second image sensor; the first optical fiber comprises a first visible light incident end close to the first scintillator layer and a first visible light emergent end far away from the first scintillator layer; the first visible light enters the first optical fiber through the first visible light incident end and exits the first optical fiber through the first visible light emergent end towards the second image sensor.

For example, in above-mentioned flat panel detector, the first light guide component further comprises a first adhesive layer, and the first optical fiber is respectively attached to the first scintillator layer and the second image sensor through the first adhesive layer.

For example, in above-mentioned flat panel detector, the first image sensor comprises: a first display region comprising a plurality of first wires; a first non-display region surrounding the first display region, wherein the first non-display region comprises a first connection part, a first connection wire corresponding to the first wire is provided in the first connection part, and the first connection wire is electrically connected with the first wire; the second image sensor comprises: a second display region comprising a second wire; a second non-display region surrounding the second display region, wherein the second non-display region comprises a second connection part, a second connection wire corresponding to a second wire is provided in the second connection part, and the second connection wire is electrically connected with the second wire; in the thickness direction of the flat panel detector, the first display region and the second display region overlap with each other, and the first connection part and the second connection part do not overlap with each other.

For example, in above-mentioned flat panel detector, the first wire comprises a first gate wire and a first data wire crossing each other, the first connection part comprises a first gate wire connection part and a first data wire connection part, the first gate wire connection part and the first data wire connection part are located at a first edge and a second edge of the first display region, respectively, and the first edge and the second edge of the first display region are adjacent to each other and connected with each other;

the second wire comprises a second gate wire and a second data wire crossing each other, the second connection part comprises a second gate wire connection part and a second data wire connection part, the second gate wire connection part and the second data wire connection part are located at a third edge and a fourth edge of the second display region, respectively, and the third edge and the fourth edge of the second display region are adjacent to and connected with each other.

For example, the above-mentioned flat panel detector further comprises: a second optical assembly, located at a side of the first image sensor far away from the first optical assembly, stacked with the first optical assembly and the first image sensor assembly and comprising a second scintillator layer configured for converting at least another part of the rays into a second visible light; a second image sensor assembly, stacked with the second optical assembly, configured for receiving the second visible light, and comprising a third image sensor located on a side of the second optical assembly far away from the first optical assembly.

For example, in above-mentioned flat panel detector, the second image sensor assembly further comprises a fourth image sensor; the second optical assembly has a third side and a fourth side opposite to the third side in the thickness direction of the flat panel detector, the fourth side is closer to the first image sensor than the third side, the third image sensor is located on the third side of the second optical assembly, and the fourth image sensor is located on the fourth side of the second optical assembly.

For example, in above-mentioned flat panel detector, the second optical assembly further comprises a second light guide component, the second light guide component is stacked with the second scintillator layer and is configured for guiding the second visible light to the second image sensor assembly.

For example, in above-mentioned flat panel detector, the second light guide component comprises a second optical fiber, and the second optical fiber is located at least on one side of the second scintillator layer in the thickness direction of the flat panel detector.

For example, in above-mentioned flat panel detector, the second optical fiber is located between the second scintillator layer and the fourth image sensor, the second optical fiber comprises a second visible light incident end close to the second scintillator layer and a second visible light emergent end far away from the second scintillator layer, and the second visible light enters the second optical fiber through the second visible light incident end and exits the second optical fiber through the second visible light emergent end towards the fourth image sensor.

For example, in above-mentioned flat panel detector, the first light guide component comprises a plurality of first optical fibers, and the second light guide component comprises a plurality of second optical fibers; the plurality of first optical fibers are tightly arranged, an included angle between a length direction of each of the plurality of first optical fibers and a plane where the first scintillator layer is located is greater than or equal to 45 degrees and less than or equal to 90 degrees, and a thickness of the first optical fiber ranges from 200 microns to 5 millimeters; the plurality of second optical fibers are tightly arranged, an comprised angle between a length direction of each of the plurality of second optical fibers and a plane where the second scintillator layer is located is greater than or equal to 45 degrees and less than or equal to 90 degrees, and a thickness of the second optical fiber ranges from 200 microns to 5 millimeters.

For example, in above-mentioned flat panel detector, a thickness of the first scintillator layer is greater than or equal to a thickness of the second scintillator layer.

For example, the above-mentioned flat panel detector further comprises a shielding assembly located between the first image sensor and the fourth image sensor and configured for shielding ultraviolet rays and electromagnetic waves with a wavelength longer than the ultraviolet rays.

For example, in above-mentioned flat panel detector, the shielding assembly comprises a shielding layer having a single-layer structure or a multi-layer structure, the shielding layer comprises a metal material, and a thickness of the shielding layer ranges from 200 microns to 5 millimeters.

For example, in above-mentioned flat panel detector, the shielding assembly further comprises a third adhesive layer, and the shielding layer is respectively attached to the first image sensor and the fourth image sensor by the third adhesive layer.

For example, in above-mentioned flat panel detector, the third image sensor comprises: a third display region comprising a plurality of third wires; a third non-display region surrounding the third display region, wherein the third non-display region comprises a third connection part, a third connection wire corresponding to the third wire is provided in the third connection part, and the third connection wire is electrically connected with the third wire; the fourth image sensor comprises: a fourth display region comprising a fourth wire; a fourth non-display region surrounding the fourth display region, wherein the fourth non-display region comprises a fourth connection part, a fourth connection wire corresponding to the fourth wire is provided in the fourth connection part, and the fourth connection wire is electrically connected with the fourth wire; in the thickness direction of the flat panel detector, the third display region and the fourth display region overlap with each other, and the third connection part and the fourth connection part do not overlap with each other.

For example, in above-mentioned flat panel detector, the third wire comprises a third gate wire and a third data wire crossing each other, the third connection part comprises a third data wire connection part and a third gate wire connection part, the third data wire connection part and the third gate wire connection part are respectively located at a fifth edge and a sixth edge of the third display region, and the fifth edge and the sixth edge of the third display region are adjacent to each other and connected with each other; the fourth wire comprises a fourth gate wire and a fourth data wire crossing each other, the fourth connection part comprises a fourth gate wire connection part and a fourth data wire connection part, the fourth gate wire connection part and the fourth data wire connection part are respectively located at a seventh edge and a eighth edge of the fourth display region, and the seventh edge and the eighth edge of the fourth display region are adjacent to each other and connected with each other.

Accordingly to second aspect of the present disclosure, it is provided a method of manufacturing a flat panel detector, comprising:

forming a first optical assembly having a first side and a second side opposite to the first side in the thickness direction of the flat panel detector, wherein the first optical assembly comprises: a first scintillator layer configured for converting at least part of rays into a first visible light; and a first light guide component stacked with the first scintillator layer and configured for guiding the first visible light;

forming a first image sensor assembly stacked with the first optical assembly and configured for receiving the first visible light, wherein the first image sensor assembly comprising a first image sensor and a second image sensor; and assembling the first image sensor, the second image sensor and the first optical assembly so that the first image sensor and the second image sensor are respectively located on the first side and the second side of the first optical assembly, so as to form a first detection unit.

For example, the above-mentioned manufacturing method comprises: forming the first image sensor, and forming the first scintillator layer on a side of the first image sensor facing the second image sensor; forming the first light guide component; forming the second image sensor, and turning the second image sensor over and rotating by 90 degrees; and assembling the first image sensor on which the first scintillator layer is formed, the first light guide component and the second image sensor that is rotated.

For example, the above-mentioned manufacturing method comprises: forming a second optical assembly, located on a side of the first image sensor far away from the first optical assembly and stacked with the first optical assembly and the first image sensor assembly, wherein the second optical assembly has a third side and a fourth side opposite to the third side in the thickness direction of the flat panel detector, the fourth side is closer to the first image sensor than the third side, and the second optical assembly comprises a second scintillator layer configured for converting at least another part of the rays into a second visible light; forming a second image sensor assembly stacked with the second optical assembly and configured for receiving the second visible light, wherein the second image sensor assembly comprises a third image sensor and a fourth image sensor; assembling the third image sensor, the fourth image sensor and the second optical assembly so that the third image sensor is located on the third side of the second optical assembly and the fourth image sensor is located on the fourth side of the second optical assembly, so as to form a second detection unit; and assembling the second detection unit and the first detection unit.

BRIEF DESCRIPTION OF THE DRAWINGS

In order to clearly illustrate the technical solution of the embodiments of the present disclosure, the drawings of the embodiments will be briefly described. It is obvious that the described drawings in the following are only related to some embodiments of the present disclosure and thus are not limitative of the present disclosure.

DETAILED DESCRIPTION

Figure 1:
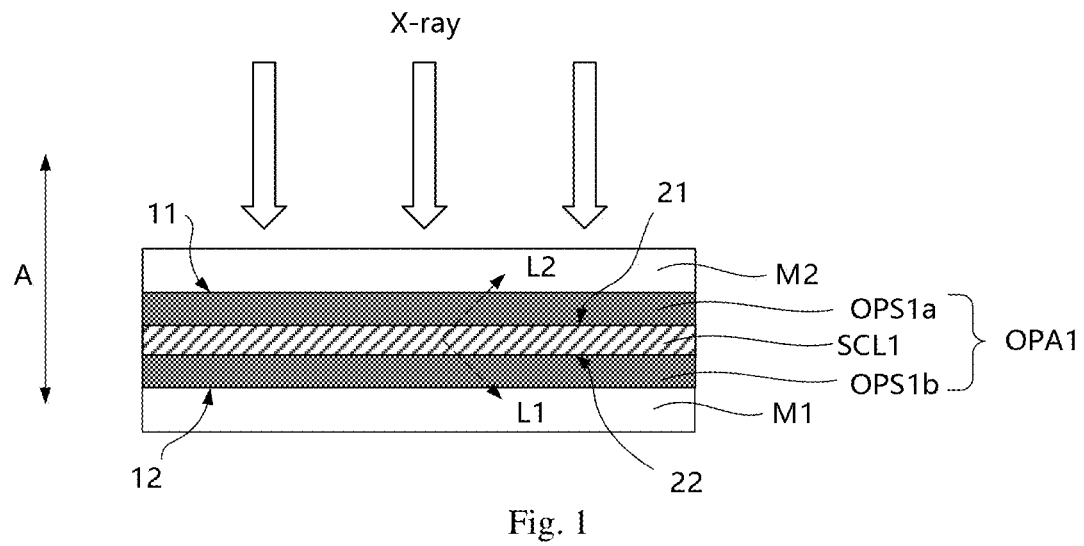
FIG. 1 is a schematic sectional view of a flat panel detector according to embodiments of the present disclosure.

In order to make objects, technical details and advantages of the embodiments of the disclosure apparent, the technical solutions of the embodiments will be described in a clearly and fully understandable way in connection with the drawings related to the embodiments of the disclosure. Apparently, the described embodiments are just a part but not all of the embodiments of the disclosure. Based on the described embodiments herein, those skilled in the art can obtain other embodiment(s), without any inventive work, which should be within the scope of the disclosure.

Unless otherwise defined, all the technical and scientific terms used herein have the same meanings as commonly understood by one of ordinary skill in the art to which the present disclosure belongs. The terms "first," "second," etc., which are used in the description and the claims of the present application for disclosure, are not intended to indicate any sequence, amount or importance, but distinguish various components. The terms "comprise," "comprising," "include," "including," etc., are intended to specify that the elements or the objects stated before these terms encompass the elements or the objects and equivalents thereof listed after these terms, but do not preclude the other elements or objects. The phrases "connect", "connected", etc., are not intended to define a physical connection or mechanical connection, but may include an electrical connection, directly or indirectly. "On," "under," "right," "left" and the like are only used to indicate relative position relationship, and when the position of the object which is described is changed, the relative position relationship may be changed accordingly.

In the existing flat panel detectors, a surficial layer of the scintillator close to the X-ray source absorbs the most X-rays and produces the strongest visible light. From the surficial surface of the scintillator into the inside of the scintillator, the intensity of X-ray becomes weaker and weaker, and the visible light generated becomes less and less. The scattering and absorption of visible light by the scintillator further weakens the intensity of the visible light moving towards the sensor. Finally, the visible light that successfully passes through the scintillator and emerges from the lower surface is absorbed by the sensor. Part of the visible light generated is emitted from the upper surface of the scintillator and cannot reach the sensor located on the lower side of the scintillator, resulting in loss of the visible light. In addition, in the medical scene, in order to reduce the harm of radiation to human body, the dose of X-ray is required to be as small as possible. However, the smaller the dose of the X-ray is, the smaller the amount of the X-ray that is detected. Therefore, it is necessary to further improve the detective quantum efficiency (DQE) of the flat panel detector to improve the detection accuracy of the flat panel detector.

The embodiments of the disclosure provide a flat panel detector. The flat panel detector includes: a first optical assembly having a first side and a second side opposite to the first side in the thickness direction of the flat panel detector. The first optical assembly includes: a first scintillator layer for converting at least part of rays into a first visible light; and a first light guide component configured to be stacked with the first scintillator layer for guiding the first visible light. The flat panel detector further includes a first image sensor assembly configured to be stacked with the first optical assembly and for receiving the first visible light. The first image sensor assembly includes: a first image sensor located at the first side of the first optical assembly; and a second image sensor located at the second side of the first optical assembly.

In the above embodiments, by arranging the second image sensor on the upper side of the first scintillator layer, part of the first visible light emitted from the upper surface of the first scintillator layer reaches the second image sensor to image, thus avoiding the loss caused by the first visible light propagating in the first scintillator layer. Further, in the above embodiments, by arranging the first light guide component stacked with the first scintillator layer in the flat panel detector, the space distance between the first image sensor and the second image sensor is increased by the first light guide component, which is beneficial to eliminate the electromagnetic interference between the first and second image sensors and improve the detection quantum efficiency (DQE) of the flat panel detector. Furthermore, in the above embodiments, the first light guide component guides the first visible light generated by the first scintillator layer to the first image sensor assembly; because the first light guide component has a limiting effect on the guided first visible light, the decrease of the modulation transfer function (MTF) of the flat panel detector is avoided, and the DQE of the flat panel detector is effectively improved or the usage dose of rays is reduced.

In the embodiments of the disclosure, the flat panel detector includes various types, for example, photodiode (PIN) type flat panel detector or metal-semiconductor-metal (MSM) type flat panel detector.

Metal-semiconductor-metal (MSM) flat panel detector receives light to reduce the resistance of semiconductor layer, thus forming a metal-insulator-semiconductor (MIS) structure, which generates a tunneling current because of electron tunneling under high voltage. A display image is obtained by collecting and detecting the tunneling current. However, the MSM flat panel detector has large dark current, low detection quantum efficiency (DQE) and low modulation transfer function (MTF).

PIN-type flat panel detector mainly includes a switching element such as a thin film transistor (TFT), and a photoelectric conversion element such as a photodiode (PIN). Under the irradiation of light such as X-ray, the scintillator layer or phosphor layer of the X-ray flat panel detector converts X-ray photons into visible light, then converts the visible light into an electrical signal under the action of PIN, and finally reads the electrical signal through the TFT and outputs the electrical signal to obtain the display image. Further, the PIN type flat panel detector includes amorphous silicon (a-Si) PIN type flat panel detector and indium gallium zinc oxide (IGZO) PIN type flat panel detector.

Taking X-ray as an example, the amorphous silicon (a-Si) PIN X-ray flat panel detector is an X-ray image detector with amorphous silicon photodiode array as core portion. For example, after the X-rays pass through the human body, the distribution of the X-rays is no longer uniform because of the different absorption degree of the X-rays by different tissues of the human body. The X-rays passing through the human body are converted into visible light by the scintillator or phosphor layer of the detector, and then the visible light is converted into the image electrical signal by the amorphous silicon array with photodiode function, and the image electrical signal is transmitted by peripheral circuits and undergoes an analog-to-digital conversion, so as to obtain the digital image. Because it has experienced the imaging process of X-ray-visible light-charge image-digital image, it is also called as indirect conversion flat panel detector. The amorphous silicon X-ray flat panel detector has the advantages of fast imaging speed, good spatial and density resolution, high signal-to-noise ratio, direct digital output and so on, so it is widely used in various digital X-ray imaging devices.

Next, the flat panel detector according to the embodiments of the disclosure will be further explained in detail by taking the flat panel detector as the amorphous silicon (a-Si) PIN X-ray flat panel detector as an example. It should be noted that in the embodiments of the disclosure, the scintillator layer is selected to be sensitive to X-ray, gamma-ray or other rays according to actual needs. In this way, the flat panel detector of the embodiments of the present disclosure can be used as an X-ray detector, a gamma-ray detector or a detector of other rays.

FIG. 1 is a schematic sectional view of the flat panel detector according to the embodiments of the present disclosure. For example, as shown in FIG. 1, the flat panel detector of the embodiments of the present disclosure includes: a first optical assembly OPA1 having a first side 11 (upper side shown in the figure) and a second side 12 (lower side shown in the figure) opposite to the first side in the thickness direction of the flat panel detector (direction A shown in the figure). The first optical assembly OPA1 includes: a first scintillator layer SCL1 for converting at least part of X-rays into a first visible light; and a first light guide component configured to be stacked with the first scintillator layer SCL1 for guiding the first visible light. The flat panel detector further includes a first image sensor assembly configured to be stacked with the first optical assembly OPA1 and configured for receiving the first visible light. The first image sensor assembly includes a first image sensor M1 located on the first side 11 of the first optical assembly OPA1; and a second image sensor M2 located on the second side 12 of the first optical assembly OPAL In the above embodiments, by arranging the second image sensor M2 on the upper side of the first scintillator layer SCL1, part of the first visible light L2 emitted from the upper surface of the first scintillator layer SCL1 reaches the second image sensor M1 to image, thus reducing the loss caused by the first visible light propagating in the first scintillator layer SCL1. Furthermore, by arranging the first light guide component OPS1 stacked with the first scintillator layer SCL1 in the flat panel detector, the space distance between the first image sensor M1 and the second image sensor M2 is increased by using the first light guide component OPS1, which is beneficial to eliminating the electromagnetic interference between the first and second image sensors M1 and M2 and improving the detection quantum efficiency (DQE) of the flat panel detector. Furthermore, in the above embodiments, the first light guide component OPS1 guides the first visible light generated by the first scintillator layer SCL1 to the first image sensor assembly. Because the first light guide component OPS1 has a limiting effect on the guided first visible light, the decrease of the Modulation Transfer Function (MTF) of the flat panel detector is avoided, the DQE of the flat panel detector is effectively improve or the usage dosage of X-rays is reduced.

In the embodiments of the disclosure, the term "stack" refers to "overlap" in the thickness direction of the flat panel detector. For example, the first image sensor assembly is configured to be stacked with the first optical assembly, which means that the first image sensor assembly and the first optical assembly partially or completely overlap with each other in the thickness direction of the flat panel detector. Further, in at least one example, the first image sensor assembly completely overlaps with the first optical assembly, so that the first image sensor assembly receives more first visible light, thereby improving the DQE of the flat panel detector, which is therefore preferable.

For example, the first light guide component is configured to be stacked with the first scintillator layer, which means that the first light guide component and the first scintillator layer partially or completely overlap with each other in the thickness direction of the flat panel detector. Furthermore, in at least one example, the first light guide component completely overlaps with the first scintillator layer, so that more of the first visible light generated by the first scintillator layer is incident into the first light guide component, thus avoiding the MTF of the flat panel detector from decreasing, which is therefore preferable.

For example, the flat panel detector includes a front side facing the user and a back side or rear side opposite to the front side, and the X-rays passing through the user's body enter the flat panel detector through the front side (incident side) of the flat panel detector. For convenience of description, in the embodiments of the disclosure, the side of the first optical assembly close to the incident side of the flat panel detector is defined as the first side, and the side of the first optical assembly facing away from the incident side of the flat panel detector is defined as the second side. Further, the image sensor located on the first side of the first optical assembly is defined as the second image sensor, and the image sensor located on the second side of the first optical assembly is defined as the first image sensor. That is, the first image sensor is far away from the incident side of the flat panel detector, while the second image sensor is close to the incident side of the flat panel detector. It should be noted that the above definitions are for illustrative purposes only, and the embodiments of the present disclosure are not limited thereto.

In the embodiments of the disclosure, the first image sensor M1 is the same as or different from the second image sensor M2 in structure. In at least one example, the first image sensor M1 and the second image sensor M2 are the same in structure, so that the manufacturing process is simplified and the complexity of circuit design is reduced, which is preferable. In the following embodiments, the first image sensor M1 and the second image sensor M2 have the same structure as an example.

In at least some embodiments, the first light guide component is located on at least one side of the first scintillator layer, that is, the first light guide component is located on one side or both sides of the first scintillator layer. In at least one example, it is preferable that the first light guide component is located on the upper side of the first scintillator layer (i.e., the side of the first scintillator layer close to the light incident side of the flat panel detector). For example, the first scintillator layer SCL1 is directly grown on the first image sensor M1, and the first light guide component is located on the upper side of the first scintillator layer; in this way, on the one hand, the lengthening of the optical path is avoided, and on the other hand, the electromagnetic interference between the first image sensor M1 and the second image sensor M2 is avoided because the first light guide component is located between the first scintillator layer and the second image sensor.

For example, as shown in FIG. 1, the flat panel detector includes the first light guide component OPS1. For example, the first light guide component OPS1 includes a first upper light guide component OPS1a and a first lower light guide component OPS1b. The first upper light guide component OPS1a is disposed on the first side 21 (upper side as shown in the figure) of the first scintillator layer SCL1 and is configured to be stacked with the first scintillator layer SCL1 in the thickness direction A of the flat panel detector. The first lower light guide component OPS1b is disposed on the second side 22 (the lower side in the figure) of the first scintillator layer SCL1 and is configured to be stacked with the first scintillator layer SCL1 in the thickness direction A of the flat panel detector.

In the embodiments of the disclosure, under X-ray irradiation, the emergent direction of the visible light excited in the scintillator is random. For example, as shown in FIG. 1, the first scintillator layer SCL1 converts X-rays into first downward visible light L1 and first upward visible light L2 that are in different directions. For example, the first downward visible light L1 is directed to the first image sensor M1, and the first upward visible light L2 is directed to the second image sensor M2. Because the first upper light guide component OPS1a is located between the first scintillator layer SCL1 and the second image sensor M2, the first upper light guide component OPS1a increases the space distance between the first image sensor M1 and the second image sensor M2, thus improving the detection quantum efficiency (DQE) of the flat panel detector. Furthermore, because the first upward visible light L2 passes through the first upper light guide component OPS1a to reach the second image sensor M2, the first upper light guide component OPS1a has a limiting effect on the first upward visible light L2, which can avoid the decrease of MTF of the flat panel detector and effectively improve the DQE of the flat panel detector.

Similarly, because the first lower light guide component OPS1b is located between the first scintillator layer SCL1 and the first image sensor M1, the first lower light guide component OPS1b further increases the space distance between the first image sensor M1 and the second image sensor M2, thus further improving the detection quantum efficiency (DQE) of the flat panel detector. Furthermore, because the first downward visible light L1 passes through the first lower light guide component OPS1b to reach the first image sensor M1, the first lower light guide component OPS1b has a limiting effect on the first downward visible light L1, which can avoid the decrease of MTF of the flat panel detector and further effectively improve the DQE of the flat panel detector.

Figure 2A:
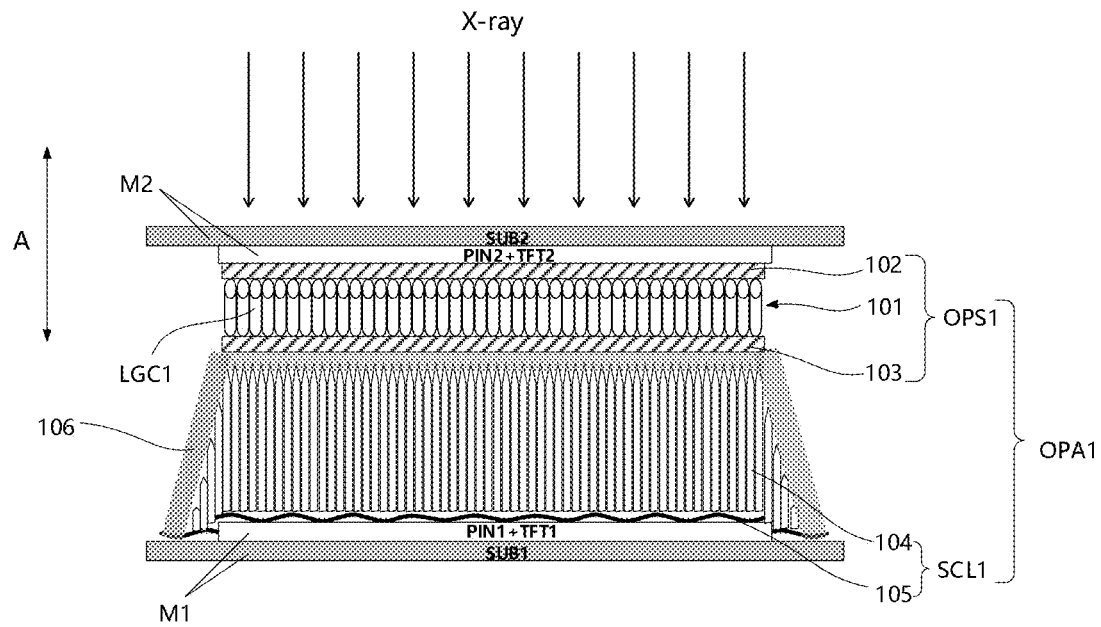
FIG. 2A is an enlarged schematic sectional view of the flat panel detector according to the embodiments of the present disclosure.

FIG. 2A is an enlarged schematic sectional view of the flat panel detector according to the embodiments of the present disclosure. Unlike FIG. 1, the flat panel detector of FIG. 2A includes a single first light guide component, and the first light guide component is located on one side of the first scintillator layer, such as the upper side as shown in the figure. That is, the first light guide component OPS1 is located between the first scintillator layer SCL1 and the second image sensor.

In at least some embodiments, the first light guide component includes a first optical fiber, and the first optical fiber is located on at least one side of the first scintillator layer in the thickness direction of the flat panel detector. In this way, the optical fiber makes use of the total reflection of light to limit the visible light it guides, thus avoiding the decrease of MTF of visible light in the transmission process and further improving the DQE of the flat panel detector. It should be noted that the optical fibers (including the first optical fiber and the second optical fiber) in the embodiments of this application have a total reflection role for visible light, but do not have a total reflection role for X-rays, gamma rays and other rays. Therefore, when the X-ray irradiates the first scintillator layer SCL1, the effect of the first optical fiber on the X-ray can be neglected.

For example, as shown in FIG. 2A, the first light guide component OPS1 includes a first optical fiber LGC1, which is located at one side of the first scintillator layer SCL1 in the thickness direction A of the flat panel detector (the upper side in the figure). In this embodiment, the first optical fiber LGC1 guides the first upward visible light L2 emitted from the upper surface of the first scintillator layer SCL1 to the second image sensor M2 by the way of total reflection. In this way, not only the loss of the first upward visible light L2 in the transmission process is reduced, but also the first upward visible light L2 is limited, so that the decrease of MTF can be avoided. It should be understood that in the case that the flat panel detector includes two first light guide components, each of which includes the first optical fiber (for example, the flat panel detector shown in FIG. 1), the first optical fiber is located on the upper and lower sides of the first scintillator layer, so that the first downward visible light L1 and the first upward visible light L2 are respectively transmitted to the first image sensor M1 and the second image sensor M2 by the way of total reflection. In this way, the loss of the first downward visible light L1 and the first upward visible light L2 in the transmission process are reduced, and both the first downward visible light L1 and the first upward visible light L2 are limited, so that the decrease of MTF can be avoided.

For example, as shown in FIG. 2A, the first scintillator layer SCL1 includes a scintillator material such as cesium iodide (CsI), gadolinium oxysulfide (GOS), or other suitable materials and structures. Further, the first scintillator layer SCL1 includes a first columnar crystal scintillator 104 and a first amorphous scintillator 105 located at the bottom of the first columnar crystal scintillator 104. According to the embodiments of the disclosure, the light scattering of the crystalline CsI in the upper part is smaller than that of the lower part (crystalline+amorphous), so that the crystalline CsI in the upper part can provide a higher MTF for the flat panel detector. Because the first image sensor M1 and the second image sensor M2 located on the upper and lower sides of the first scintillator layer SCL1 jointly receive the visible light, the sensitivity of the flat panel detector is further improved.

Figure 3:
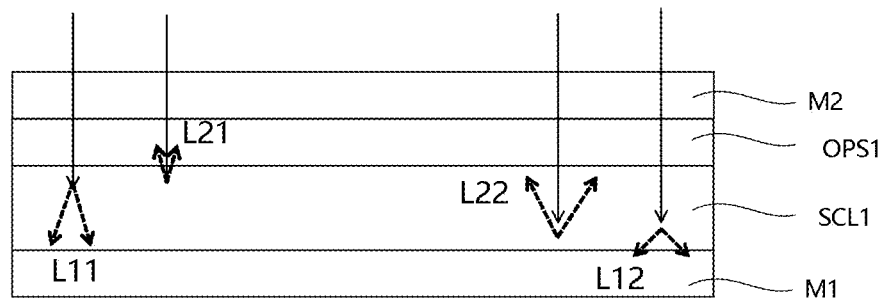
FIG. 3 is a schematic view of an optical path of the flat panel detector according to the embodiments of the disclosure.

FIG. 3 is a schematic view of an optical path of the flat panel detector according to the embodiments of the disclosure. As shown in FIG. 3, X-rays are incident on the first scintillator layer SCL1, the first scintillator layer SCL1 converts the X-rays into the first downward visible light L1 and the first upward visible light L2. For example, the first downward visible light L1 includes a visible light L11 converted by the upper part of the first scintillator layer SCL1 and a visible light L12 converted by the lower part of the first scintillator layer SCL1. For example, the first upward visible light L2 includes a visible light L21 converted by the upper part of the first scintillator layer SCL1 and a visible light L22 converted by the lower part of the first scintillator layer SCL1. The visible light L21, L22 enters the second image sensor M2 through the first optical fiber LGC1 in the first light guide component. The visible light L21 and L22 both is transmitted to the second image sensor M2 by way of total reflection, so that the first optical fiber LGC1 has a limiting effect on the visible light L21 and L22, thereby avoiding the decrease of MTF and improving the DQE of the flat panel detector.

Figure 4:
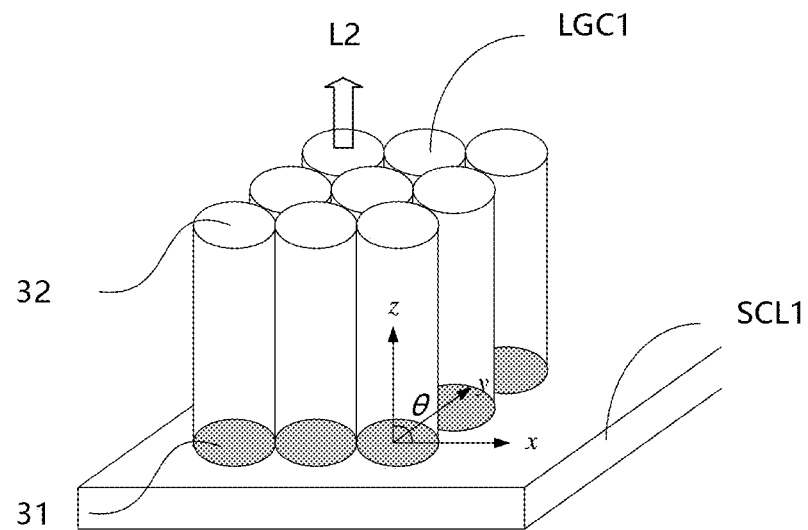
FIG. 4 is a structural schematic view of an optical fiber in the flat panel detector according to the embodiments of the disclosure.

For example, as shown in FIG. 2A, the first optical fiber LGC1 is located between the first scintillator layer SCL and the second image sensor M2. FIG. 4 is a structural schematic view of the optical fiber in the flat panel detector according to the embodiments of the disclosure. For example, as shown in FIG. 4, the first optical fiber LGC1 includes a first visible light incident end 31 close to the first scintillator layer SCL1 and a first visible light emergent end 32 far away from the first scintillator layer SCL1, so that the first upward visible light L2 including visible light L21 and L22 enters the first optical fiber LGC1 through the first visible light incident end 31 and exits through the first visible light emergent end 32 towards the second image sensor M2. In this way, because the first visible light incident end 31 is tightly close to the first scintillator layer SCL1, the first upward visible light L2 generated by the first scintillator layer SCL1 directly enters the first optical fiber LGC1 through the first visible light incident end 31, which can not only reduce the light loss of the first upward visible light L2, but also limit the first upward visible light L2, avoid decrease of MTF and improve the DQE of the flat panel detector. For example, as shown in FIG. 4, the first light guide component includes a plurality of first optical fibers LGC1, which are tightly arranged. For example, in the plane where the first scintillator layer SCL1 is located (the xy plane shown in the figure), the plurality of the first optical fibers LGC1 are arranged in an array, and two adjacent first optical fibers LGC1 are in contact with each other. In this way, the gaps between the first optical fibers can be reduced, and the light loss of visible light in the transmission process can be further reduced.

In at least some embodiments, an included angle between a length direction of each first optical fiber (and the second optical fiber in later embodiments) and the plane of the first scintillator layer or the second scintillator layer is greater than or equal to 45 degrees and less than or equal to 90 degrees. In this way, the first upward visible light L2 is made to propagate in substantially the same direction, that is, toward the second image sensor M2, thereby allowing the second image sensor M2 collect more first upward visible light L2.

For example, as shown in FIG. 4, the included angle θ between the length direction (Z direction shown in the figure) of each first optical fiber LGC1 and the plane (xy plane shown in the figure) of the first scintillator layer SCL1 is 90 degrees. In this way, the length of the optical path of the first upward visible light L2 is reduced and the light loss is reduced, which therefore is preferable. In at least one example, a thickness of the first optical fiber LGC1 ranges from 200 microns to 5 millimeters. In at least one example, the thickness of the first optical fiber is regarded as the thickness of the optical fiber layer composed of the first optical fiber. For example, as shown in FIG. 2A, the plurality of first optical fibers LGC1 constitute a first optical fiber layer 101, and the thickness of the first optical fiber layer 101 ranges from 200 microns to 5 millimeters.

In at least some embodiments, the first light guide component further includes a first adhesive layer, through which the first optical fiber is attached to the first scintillator layer and the second image sensor, respectively.

For example, as shown in FIG. 2A, the first light guide component OPS1 further includes a first upper adhesive layer 102 and a first lower adhesive layer 103. For example, the first upper adhesive layer 102 is located on the upper side of the first optical fiber LGC1, and the first optical fiber LGC1 is attached to the second image sensor M2 through the first upper adhesive layer 102. For example, the first lower adhesive layer 103 is located on the lower side of the first optical fiber LGC1, and the first optical fiber LGC1 is attached to the first scintillator layer SCL1 through the first lower adhesive layer 103. In at least one example, in order to reduce the influence on the optical path, the first upper adhesive layer 102 and the first lower adhesive layer 103 include optically transparent adhesive OCA.

For example, as shown in FIG. 2A, the flat panel detector further includes a first encapsulation layer 106 that seals at least the first image sensor M1 and the first scintillator layer SCL1. In this way, it is possible to prevent water vapor or impurities from entering the first image sensor M1 and the first scintillator layer SCL1 to affect the image quality. In addition, the first image sensor M1 and the first scintillator layer SCL1 are packaged together, which also facilitates the assembly of the flat panel detector subsequently.

Figure 2B:
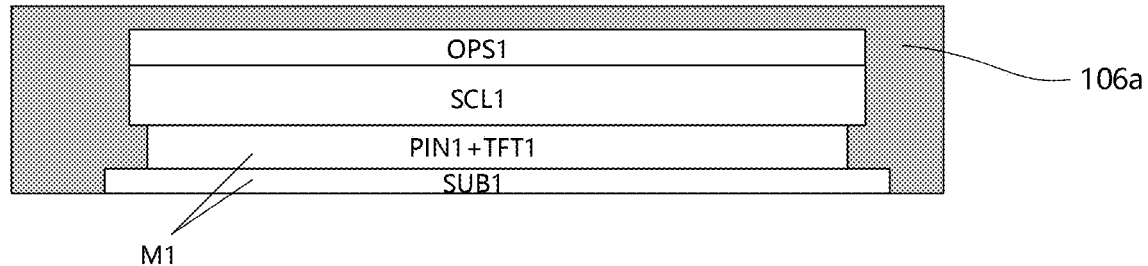
FIG. 2B is a structural schematic view of a encapsulation layer in the flat panel detector according to the embodiments of the disclosure.

FIG. 2B is a structural schematic view of the encapsulation layer in the flat panel detector according to the embodiments of the disclosure. For example, as shown in FIG. 2B, the first encapsulation layer 106a seals the first image sensor M1, the first light guide component OPS1 and the first scintillator layer SCL1. In this way, it is possible to prevent water vapor or impurities from entering the first image sensor M1, the first light guide component OPS1 and the first scintillator layer SCL1 to affect the image quality. In at least some embodiments, the encapsulation layer is made of transparent material to avoid the influence on light. For example, the encapsulation layer includes an organic light-transmitting material or an inorganic light-transmitting material. For example, the encapsulation layer has a single-layer structure or a multi-layer structure.

Figure 5:
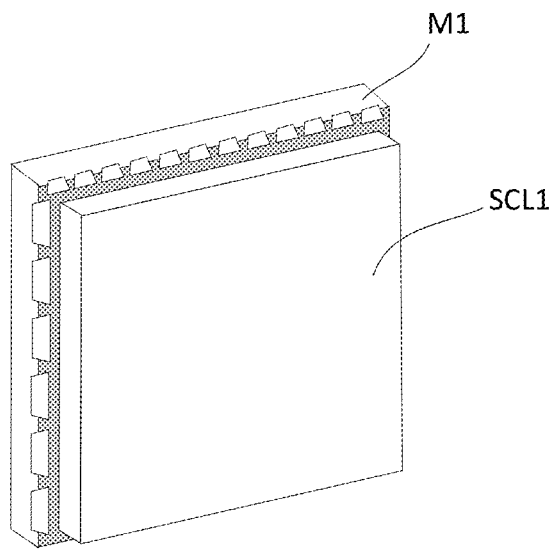
FIG. 5 is a schematic view of a three-dimensional structure of a first image sensor and a first scintillator layer according to the embodiments of the disclosure.
Figure 6A:
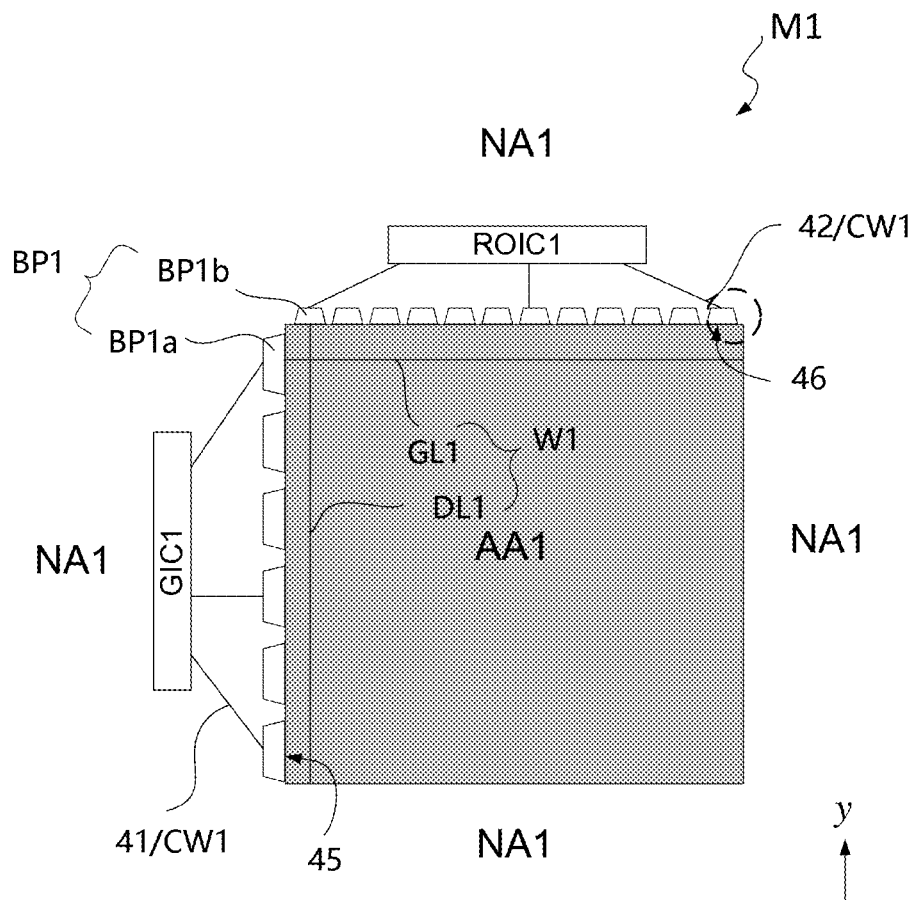
FIG. 6A is a schematic plan view of the first image sensor according to the embodiments of the disclosure.
Figure 7:
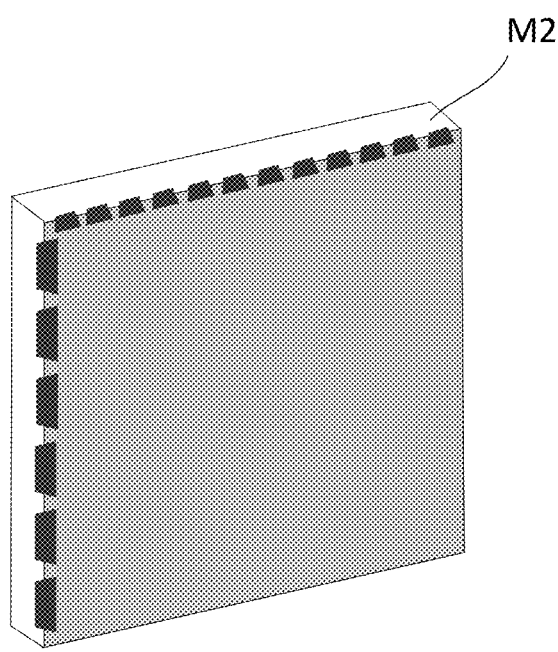
FIG. 7 is a schematic view of a three-dimensional structure of a second image sensor according to the embodiments of the disclosure.
Figure 8A:
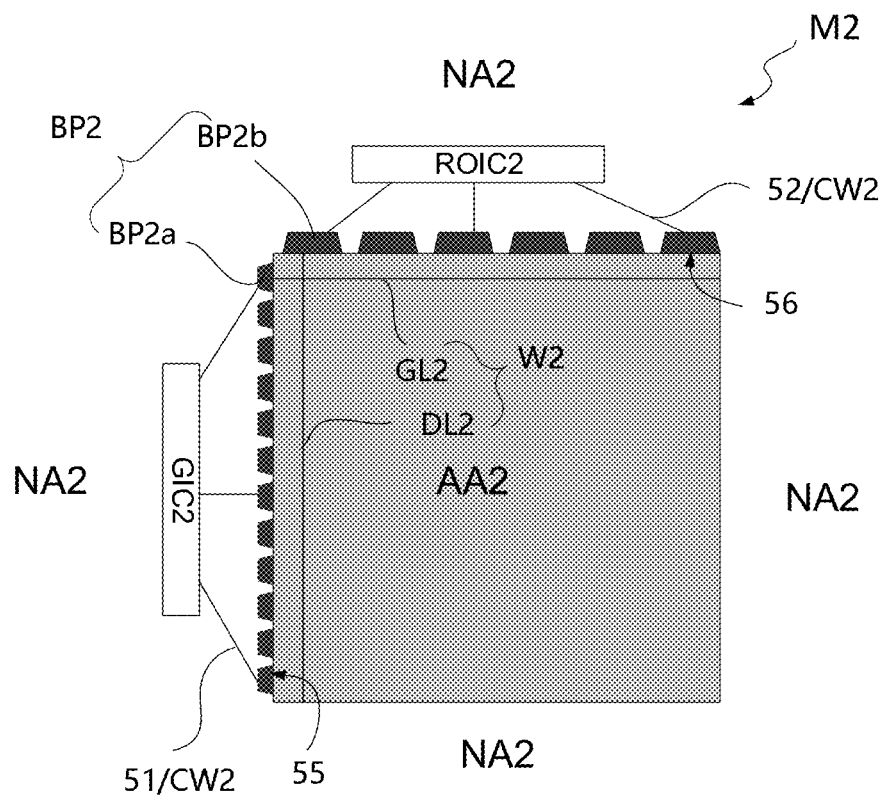
FIG. 8A is a schematic plan view of the second image sensor according to the embodiments of the disclosure.
Figure 8B:
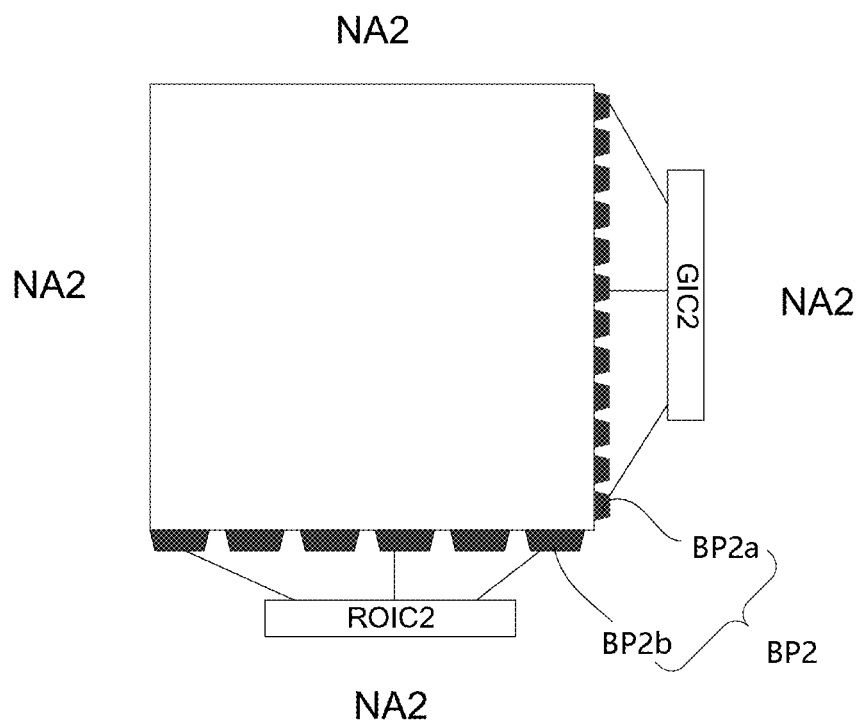
FIG. 8B is a schematic plan view of the second image sensor of FIG. 8A after being turned over and rotated by 90 degrees.

FIG. 5 is a schematic view of a three-dimensional structure of the first image sensor and the first scintillator layer according to the embodiments of the disclosure. FIG. 6A is a schematic plan view of the first image sensor according to the embodiments of the disclosure. FIG. 7 is a schematic view of a three-dimensional structure of the second image sensor according to the embodiments of the disclosure. FIG. 8A is a schematic plan view of the second image sensor according to the embodiments of the disclosure. FIG. 8B is a schematic plan view of the second image sensor of FIG. 8A after being turned over and rotated by 90 degrees.

For example, as shown in FIGS. 5 and 6A, the first image sensor M1 includes a first display region AA1 for displaying image. The first display region AA1 includes a plurality of first wires W1. The first image sensor M1 further includes a first non-display region NA1 surrounding the first display region AA1. The first non-display region NA1 is not used for displaying image, and for example it is provided with connection wires, contact pads, integrated circuits and the like for electrically connecting the first wire W1 of the first display region AA1 to an external control circuit. For example, as shown in FIG. 6A, the first non-display region NA1 includes a first connection part BP1, in which a first connection wire CW1 corresponding to the first wire W1 is provided, and the first connection wire CW1 is electrically connected with the first wire W1.

For example, as shown in FIGS. 7 and 8A, the second image sensor includes a second display region AA2 including a second wire W2. The second image sensor M2 further includes a second non-display region NA2 surrounding the second display region AA2. The second non-display region NA2 is not used for displaying image, and for example it is provided with connection wires, contact pads, integrated circuits and the like for electrically connecting the second wire W2 of the second display region AA2 to an external control circuit. For example, as shown in FIG. 8A, the second non-display region AA2 includes a second connection part BP2 in which a second connection wire CW2 corresponding to the second wire W2 is provided, and the second connection wire CW2 is electrically connected with the second wire W2.

In at least some embodiments, the first scintillator layer SCL1 is directly grown on or attached to the first image sensor M1. In at least one example, the first scintillator layer SCL1 is directly grown on the first image sensor M1, resulting in the structure shown in FIG. 5. In the case that the first scintillator layer SCL1 is attached to the first image sensor M1, the optical path is lengthened, which reduces MTF, DQE, etc. Therefore, it is preferable that the first scintillator layer SCL1 is directly grown on the first image sensor M1; in this case, the first light guide component is not provided between the first scintillator layer SCL1 and the first image sensor M1. Then, the first light guide component OPS1, the first image sensor M1 with the first scintillator layer SCL1 in FIG. 5 and the second image sensor M2 in FIG. 8B are assembled together to form the final flat panel detector.

Figure 9:
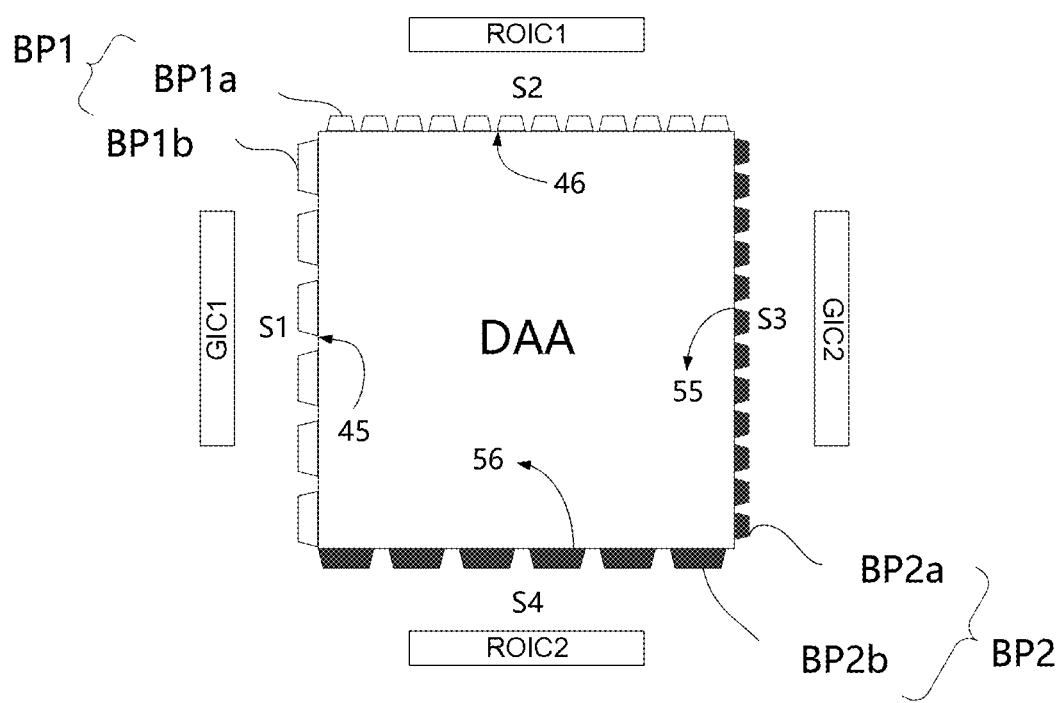
FIG. 9 is a schematic plan view of the flat panel detector after being assembled according to the embodiments of the disclosure.

FIG. 9 is a schematic plan view of the flat panel detector after being assembled according to the embodiments of the disclosure. For example, as shown in FIG. 9, in the thickness direction A of the flat panel detector, the first display region AA1 and the second display region AA2 overlap with each other, and the first connection part BP1 and the second connection part BP2 do not overlap with each other. In this way, the signals on the respective external control circuits (including the driving circuit and the readout circuit) of the first image sensor M1 and the second image sensor M2 do not interfere with each other, thus improving the sensitivity and integration of the flat panel detector.

It should be noted that the first connection part BP1 and the second connection part BP2 do not overlap with each other, which means that the orthographic projection of the first connection part BP1 on the plane of the substrate does not overlap with that of the second connection part BP2 on the plane of the substrate. That is, the orthographic projection of the first connection part BP1 on the plane of the substrate is located outside the orthographic projection of the second connection part BP2 on the plane of the substrate, and the orthographic projection of the second connection part BP2 on the plane of the substrate is located outside the orthographic projection of the first connection part BP1 on the plane of the substrate. Here, only the expression that "the first connection part BP1 and the second connection part BP2 do not overlap with each other" is explained as an example. It can be understood that as for the expression that any two layers, two circuits and two regions do not overlap with each other in the embodiments of the present disclosure, it can be understood with reference to the above manner, and will not be explained one by one in the embodiments of the present disclosure. For example, as shown in FIG. 2A, the substrate is a first substrate SUB1 of the first image sensor M1 or a second substrate SUB2 of the second image sensor M2.

For example, as shown in FIG. 6A, the first image sensor M1 further includes a first driving circuit GIC1 and a first readout circuit ROIC1 disposed in the first non-display region NA1. For example, the first connection wire CW1 includes a first gate connection wire 41 that electrically connects the first gate wire GL1 to the first driving circuit GIC1. The first driving circuit GIC1 provides a driving signal to the first gate wire GL1. For example, the first connection wire CW1 further includes a first data connection wire 42, which electrically connects the first data wire DL1 to the first readout circuit ROIC1. The first readout circuit ROIC1 reads the electrical signal generated by each first sensing region in the first image sensor M1.

Figure 6B:
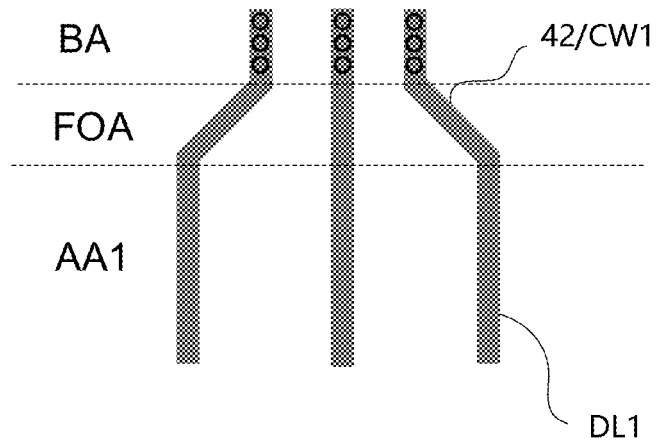
FIG. 6B is a partially enlarged schematic view of a first binding region of the first image sensor according to the embodiments of the disclosure.

FIG. 6B is a partially enlarged schematic view of a first binding region of the first image sensor according to the embodiments of the disclosure. For example, FIG. 6B is an enlarged schematic view of the first data wire binding part of the dashed circle of FIG. 6A. As shown in FIG. 6B, the first non-display region NA1 includes a fan-out region FOA close to the first display region AA1 and a binding region located on a side of the fan-out region FOA far away from the first display region AA1. The fan-out region FOA gathers a plurality of first data connection wires 42. The bonding region includes a plurality of contact pads (shown as circles in the figure) for electrically connecting the first data connection wires 42 to the external circuit. For example, each first data wire binding part includes a plurality of first data connection wires 42 (three are shown in the figure), and the first data connection wires 42 correspond to the first data wires DL1 one by one. In this way, the electric signal obtained on each first data wire DL1 is transmitted to the first readout circuit ROIC1.

For example, as shown in FIGS. 8A and 8B, the second image sensor M1 further includes a second driving circuit GIC2 and a second readout circuit ROIC2 provided in the second non-display region NA1. For example, the second connection wire CW2 includes a second gate connection wire 51 that electrically connects the second gate wire GL2 to the second driving circuit GIC2. The second driving circuit GIC2 supplies a driving signal to the second gate wire GL2. For example, the second connection wire CW2 further includes a second data connection wire 52 that electrically connects the second data wire DL2 to the second readout circuit ROIC2. The second readout circuit ROIC2 reads the electrical signal generated by each second sensing region in the second image sensor M2.

For example, as shown in FIG. 9, the first driving circuit GIC1 and the second driving circuit GIC2 do not overlap with each other in the thickness direction A of the flat panel detector. Furthermore, the first driving circuit GIC1 and the second driving circuit GIC2 are respectively located at opposite sides of the first display region AA1 (or the second display region AA2). In this way, signal interference between the first driving circuit GIC1 and the second driving circuit GIC2 can be avoided.

For example, as shown in FIG. 9, the first readout circuit ROIC1 and the second readout circuit ROIC2 do not overlap with each other in the thickness direction A of the flat panel detector. Further, the first readout circuit ROIC1 and the second readout circuit ROIC2 are respectively located at opposite sides of the first display region AA1 (or the second display region AA2). In this way, signal interference between the first readout circuit ROIC1 and the second readout circuit ROIC2 can be avoided.

Further, for example, in the flat panel detector shown in FIG. 9, first display region AA1 and second display region AA2 completely overlapping with each other are collectively referred to as the detection display region DAA, which includes a first side S1, a second side S2, a third side S3 and a fourth side S4; the first side S1 is opposite to the third side S3, and the second side S2 is opposite to the fourth side S4. For example, as shown in FIG. 9, the first driving circuit GIC1 and the second driving circuit GIC2 are located on the first side S1 and the third side S3 of the detection display region DAA, respectively. For example, as shown in FIG. 9, the first readout circuit ROIC1 and the second readout circuit ROIC2 are located on the second side S2 and the fourth side S4 of the detection display region DAA, respectively. In this way, signal interference between the first readout circuit ROIC1 (or the second readout circuit ROIC2) and the first drive circuit GIC1 (or the second drive circuit GIC2) in the flat panel detector can be avoided.

For example, as shown in FIG. 6A, the first connection part BP1 includes a first gate wire connection part BP1a and a first data wire connection part BP1b, which are located at the first edge 45 and the second edge 46 of the first display region AA1, respectively, and the first edge 45 and the second edge 46 are adjacent to each other and connected to each other. For example, as shown in FIG. 8A, the second connection part BP2 includes a second gate wire connection part BP2a and a second data wire connection part BP2b, which are located at the third edge 55 and the fourth edge 56 of the second display region AA2, respectively, and the third edge 55 and the fourth edge 56 are adjacent to each other and connected to each other. Thus, as shown in FIG. 9, in the case that the second image sensor M2 after being turned over and rotated by 90 degrees, is combined with the first image sensor M1, the first edge 45 and the third edge 55 are located on the first side S1 and the third side S3 of the detection display region DAA, and the second edge 46 and the fourth edge 56 are located on the second side S2 and the fourth side S4 of the detection display region DAA, respectively. With the above arrangement, it is avoided that the second connection wire W2, the second connection part BP2, the second driving circuit GIC2 and the second readout circuit ROIC2 of the second image sensor M2 and the first connection wire W1, the first connection part BP1, the first driving circuit GIC1 and the first readout circuit ROIC1 of the first image sensor M1 overlap with each other, thereby avoiding the interference of signals between the two image sensors.

For example, as shown in FIG. 6A, the first wire W1 includes a first gate wire GL1 and a first data wire DL1 crossing each other. In at least one example, there are a plurality of first gate wires GL1 and a plurality of first data wires DL1, which cross each other to form a plurality of first photosensitive regions. For example, as shown in FIG. 8A, the second wire W2 includes a second gate wire GL2 and a second data wire DL2 crossing each other. In at least one example, there are a plurality of second gate wires GL2 and a plurality of second data wires DL2, which cross each other to form a plurality of second photosensitive regions.

Figure 10:
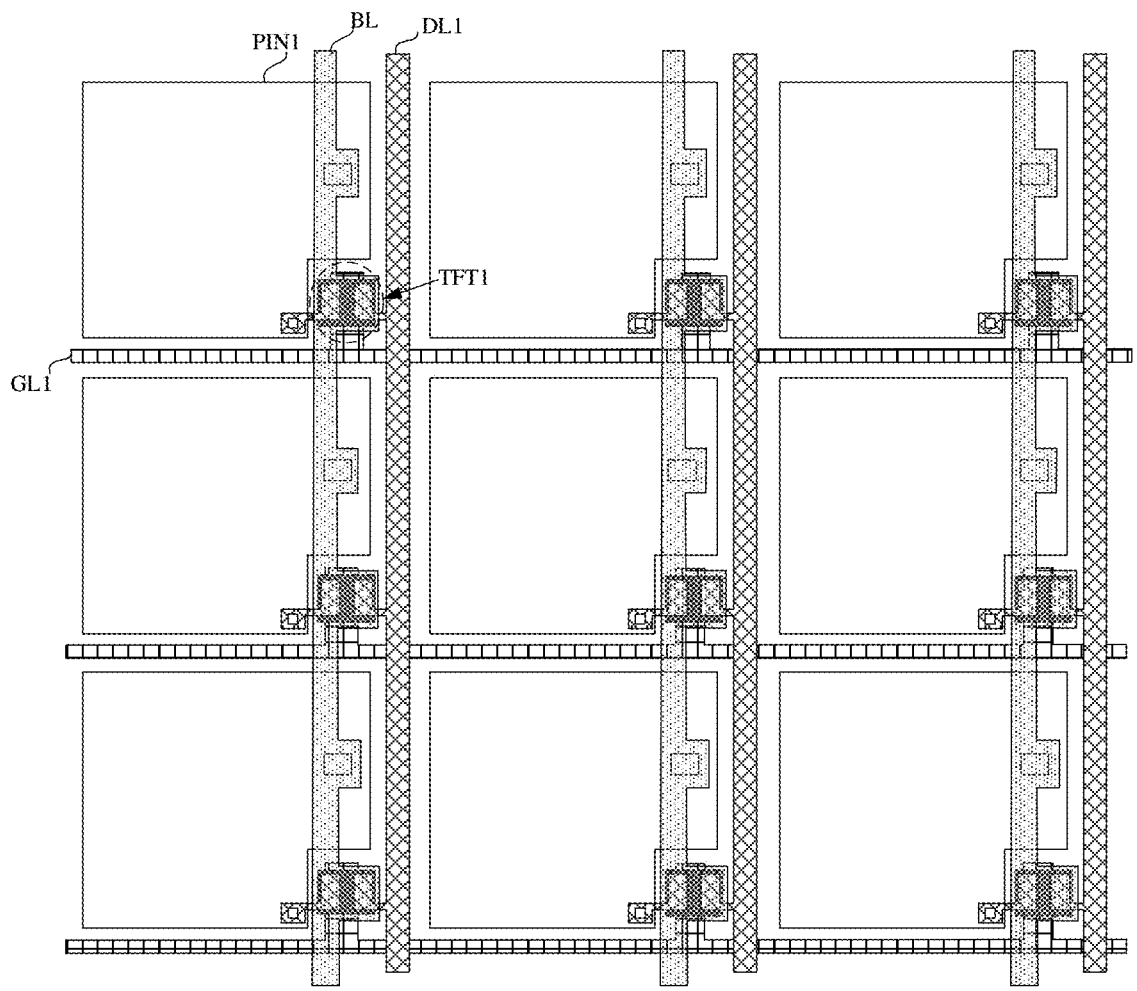
FIG. 10 is a partial schematic circuit diagram of the first image sensor according to the embodiments of the disclosure.
Figure 11:
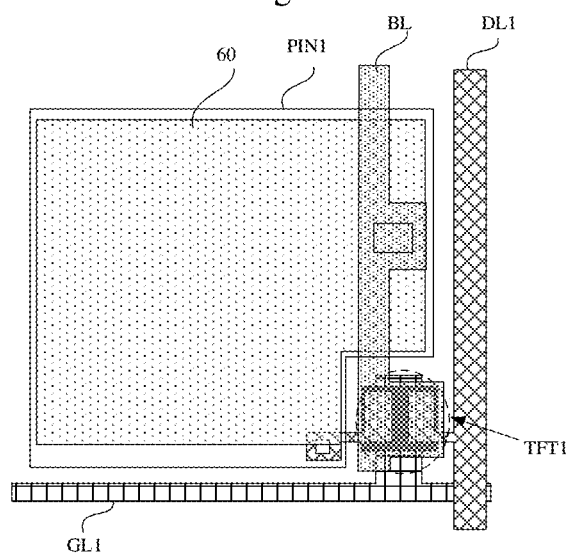
FIG. 11 is a schematic circuit diagram of a first photosensitive region of the first image sensor according to the embodiments of the disclosure.
Figure 12:
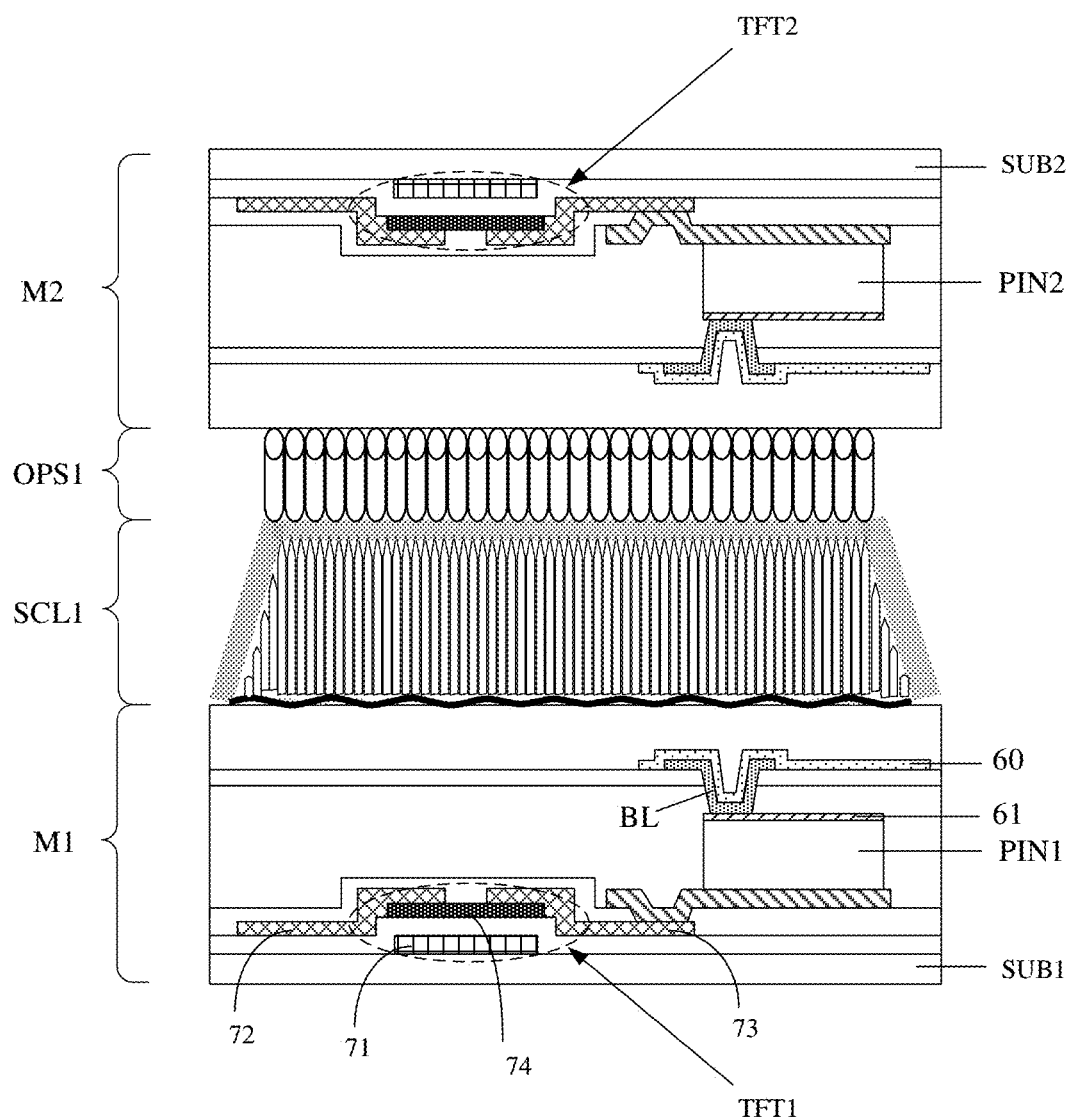
FIG. 12 is another enlarged schematic sectional view of the flat panel detector according to the embodiments of the present disclosure.

As mentioned above, the first image sensor M1 and the second image sensor M2 in the embodiments of the present disclosure have the same structure, so the specific structure of the image sensor M1 will be described in detail below. FIG. 10 is a partial schematic circuit diagram of the first image sensor according to the embodiments of the disclosure. FIG. 11 is a schematic circuit diagram of the first photosensitive region of the first image sensor according to the embodiments of the disclosure. FIG. 12 is another enlarged schematic sectional view of the flat panel detector according to the embodiments of the present disclosure. For example, as shown in FIG. 12, the second image sensor M2 has the same structure as the first image sensor M1, and they are symmetrically distributed with respect to the middle part of the flat panel detector (including the first scintillator layer SCL1 and the first light guide component OPS1).

For example, as shown in FIGS. 10 and 11, the first image sensor M1 includes the first substrate SUB1 and the plurality of first gate wires GL1 and the plurality of first data wires DL1 disposed on the first substrate SUB1. For example, the plurality of first gate wires GL1 and the plurality of first data wires DL1 cross each other to form the plurality of first photosensitive regions which are arranged in an array. For example, the first photosensitive region array arranged in a 3×3 array.

For example, as shown in FIG. 11 and FIG. 12, each first photosensitive region is similar to a pixel region of the liquid crystal display region, and includes a first photodiode PIN1 and a first thin film transistor TFT1, the first thin film transistor TFT1 serves as a switching element and the first photodiode PIN1 serves as a photoelectric conversion element. For example, the first thin film transistor TFT1 includes a gate electrode 71, a source electrode 72, a drain electrode 73, and an active layer 74. The gate electrode 71 of the first TFT1 is connected to the first gate wire GL1 of the first image sensor M1, the drain electrode 72 of the first TFT1 is connected to the first data wire DL1 of the first image sensor M1, and the source electrode 73 of the first TFT1 is connected to the photodiode PIN1. In the embodiments of the disclosure, the positions of the source electrode 72 and the drain electrode 73 can be replaced with each other.

The first image sensor M1 controls the switching state of the first thin film transistor TFT1 through the first driving circuit GIC1. In the case that the first thin film transistor TFT1 is turned on, the photocurrent signal generated by the first photodiode PIN1 is read out through the first data wire DL1 connected to the first thin film transistor TFT1 and the first reading circuit ROIC1 in turn. The acquisition of photoelectric signal is completed by controlling the signal timing on the first gate wire GL1 and the first data wire DL1, that is, the acquisition of photocurrent signal generated by the first photodiode PIN1 is completed by controlling the switching state of the first thin film transistor TFT1.

More specifically, during the first image sensor M1 works, each first photosensitive region receives the optical signal and converts it into an electrical signal, which is stored in a storage capacitor or a capacitance of the first photodiode PIN1 itself. The first photodiode PIN1 receives the visible light converted by the first scintillator layer SCL1, and generates photo-generated carriers which are converted into the electric signal proportional to the intensity of the visible light. The first driving circuit GIC1 is connected to the array of the first photosensitive regions, controls the gate electrodes of the first thin film transistors TFT1 in each row, and controls the connection or disconnection between the source electrode and the drain electrode of the first thin film transistors TFT1 by voltage applied to the gate electrode, so that the respective first photosensitive regions are turned on row by row. The first reading circuit ROIC1 is connected to the array of the first photosensitive region, and reads the charges in the first photosensitive region of the same row under the condition that the first thin film transistors TFT1 of the same row are turned on, so as to read the image information. Generally, the size of the first photosensitive region determines the imaging resolution. Therefore, the smaller the region of the first photosensitive region is, the higher the resolution of the image is.

For example, as shown in FIGS. 10 to 12, the first image sensor M1 further includes a signal wire BL, which is arranged on the side of the first photodiode PIN1 far away from the first substrate SUB1 and connected with the first photodiode PIN1. The signal wire BL is used to provide a voltage signal to the first photodiode PIN1. For example, the first image sensor M1 further includes a transmissive conductive layer 60 disposed on the side of the first photodiode PIN1 far away from the first substrate SUB1. A constant voltage is input to the conductive layer 60, so that the conductive layer 60 blocks external static electricity and prevents the external static electricity from influencing the first photodiode PIN1. In at least one example, the transmissive conductive layer 60 is made of a light-transmissive conductive material, so that light is transmitted to the first photodiode PIN1. For example, a conductive material with a transmittance over 50% is selected, for example, the transparent conductive material is selected, which includes but is not limited to IZO (Indium Zinc Oxide), ITO (Indium Tin Oxide), AZO (aluminum zinc oxide), IFO (Indium FOxide), etc.

For example, as shown in FIGS. 11 and 12, in order to improve the signal receiving effect of the photodiode 11, as shown in FIG. 3, a transparent conductive layer 61 is provided on the side of the photodiode 11 close to the signal wire 19 to increase the contact region between the signal wire 19 and the photodiode 11. For example, the transparent conductive layer 61 is made of a conductive material with a transmittance over 50%, for example, the transparent conductive material includes but is not limited to IZO (Indium Zinc Oxide), ITO (Indium Tin Oxide), AZO (aluminum zinc oxide), IFO (Indium FOxide), etc. The materials of the transparent conductive layer 61 and the transmissive conductive layer 60 may be the same or different, which is not limited by the embodiments of the present disclosure.

In the following embodiments, for convenience of description, the structure including an image sensor assembly (at least one image sensor) and a scintillator layer will be referred to as a detection unit. Therefore, the flat panel detectors shown in FIGS. 1, 2A, 9 and 12 all have a single detection unit.

In at least some embodiments, the flat panel detector has dual detection units, which further improves the MTF and sensitivity of the flat panel detector, thus further improving the image quality.

Figure 13:
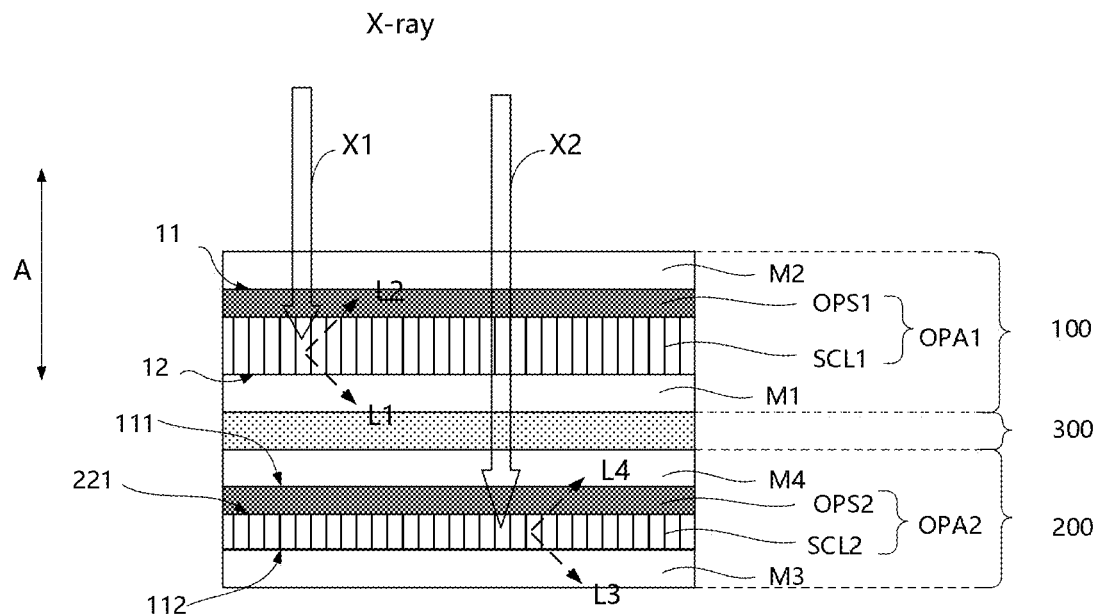
FIG. 13 is still another schematic enlarged sectional view of the flat panel detector according to the embodiments of the present disclosure.

FIG. 13 is still another schematic enlarged sectional view of the flat panel detector according to the embodiments of the present disclosure. For example, as shown in FIG. 13, the flat panel detector of the embodiments of the present disclosure includes a first detection unit 100 and a second detection unit 200, which are stacked in the thickness direction a of the flat panel detector. In at least one example, the second detection unit 200 is located on the opposite side of the X-ray incident side of the first detection unit 100. For illustrative purposes, FIG. 13 shows that the first detection unit 100 is located above the second detection unit 200. It can be understood that in the case that X-rays are incident from the lower side of the first detection unit 100, the second detection unit 200 is located above the first detection unit 100, which also achieve the purpose of the present disclosure.

For example, as shown in FIG. 13, the first detection unit 100 includes the first optical assembly OPA1 having the first side 11 (upper side shown in the figure) and the second side 12 (lower side shown in the figure) opposite to the first side in the thickness direction of the flat panel detector (direction A shown in the figure). The first optical assembly OPA1 includes: the first scintillator layer SCL1 for converting at least part of X-rays (X1 rays shown in the figure) into the first visible light (including the first downward visible light L1 and the first upward visible light L2); and the first light guide component OPS1 configured to be stacked with the first scintillator layer SCL1 for guiding the first visible light. The first detection unit 100 further includes the first image sensor assembly configured to be stacked with the first optical assembly OPA1 and configured to receive the first visible light. The first image sensor assembly includes: the first image sensor M1 located on the first side 11 of the first optical assembly OPA1; and the second image sensor M2 located on the second side 12 of the first optical assembly OPA1.

For example, as shown in FIG. 13, the second detection unit 200 includes: a second optical assembly OPA2 located on the side of the first image sensor M1 away from the first optical assembly OPA1 and configured to be stacked with the first optical assembly OPA1 and the first image sensor assembly. The second optical assembly OPA2 includes a second scintillator layer SCL2 for converting at least another part of X rays (X2 rays shown in the figure) into a second visible light (including a second downward visible light L3). The second detection unit 200 further includes a second image sensor assembly configured to be stacked with the second optical assembly OPA2 for receiving the second visible light. The second image sensor assembly includes: a third image sensor M3 located on the side of the second optical assembly OPA2 far away from the first optical assembly OPAL For example, the first scintillator layer SCL1 converts most of the X-rays, such as X1 rays, into the first visible light. However, in actual products, the absorption ratio of the scintillator for X-rays ranges from about 30% to 60%, so that after passing through the first scintillator layer SCL1, a considerable proportion of X-ray information is still not effectively read. In the above embodiments, because the flat panel detector has dual detection units, the first scintillator layer SCL-1 converts the X1 rays irradiated on it into the first visible light, and the second scintillator layer SCL-2 converts the X2 rays of the X rays that have not been converted by the first scintillator layer SCL-1 into the second visible light, and then the second visible light is collected by the third image sensor M3. Compared with the flat panel detector with a single detection unit, the flat panel detector of the above embodiments collects more X-rays, obtain more complete image information, and further improve the MTF and sensitivity of the flat panel detector, thereby obtaining better image quality.

For convenience of description, in the embodiments of the disclosure, the side of the second optical assembly close to the incident side of the flat panel detector is defined as the fourth side, and the side of the second optical assembly far away from the incident side is defined as the third side. Further, the image sensor located on the third side of the second optical assembly is defined as the third image sensor, and the image sensor located on the fourth side of the second optical assembly is defined as the fourth image sensor. That is, the fourth image sensor is close to the incident side of the flat panel detector, while the third image sensor is far away from the incident side of the flat panel detector. It should be noted that the above definitions are for illustrative purposes only, and the embodiments of the present disclosure are not limited thereto.

For example, as shown in FIG. 13, the second image sensor assembly further includes a fourth image sensor M4. The second optical assembly OPA2 has a third side 112 (lower side shown in the figure) and a fourth side 111 (upper side shown in the figure) opposite to the third side 112, and the fourth side 111 is closer to the first image sensor M1 than the third side 112. For example, the third image sensor M3 is located on the third side 112 of the second optical assembly OPA2, and the fourth image sensor M4 is located on the fourth side 111 of the second optical assembly OPA2.

Referring to the description of the first scintillator layer SCL1 in the previous embodiments, the direction of the second visible light converted by the second scintillator layer SCL2 is random, for example, the second visible light includes the second downward visible light L3 and the second upward visible light L4. In the above embodiments, by arranging the fourth image sensor M4 on the upper side of the second scintillator layer SCL2, part of the second visible light L4 emitted from the upper surface of the second scintillator layer SCL2 reaches the fourth image sensor M4 to image, thus reducing the loss caused by propagating process of the second visible light in the scintillator layer. Furthermore, because more second visible light is obtained, more complete image information is obtained.

In the embodiments of the disclosure, the second optical assembly may or may not include a second light guide component. In the case that the second optical assembly includes the second light guide component, the second light guide component limits the second visible light generated by the second scintillator layer, thus avoiding the decrease of MTF of the flat panel detector, and further effectively improving the DQE of the flat panel detector, which therefore is preferable.

In the embodiments of the disclosure, the third image sensor M3 and the fourth image sensor M4 are the same or different in structure. In at least one example, in the case that the third image sensor M3 and the fourth image sensor M4 are same in structure, the manufacturing process is simplified and the complexity of circuit design is reduced, which therefore is preferable. In the following embodiments, the third image sensor M3 and the fourth image sensor M4 have the same structure as an example.

Figure 14:
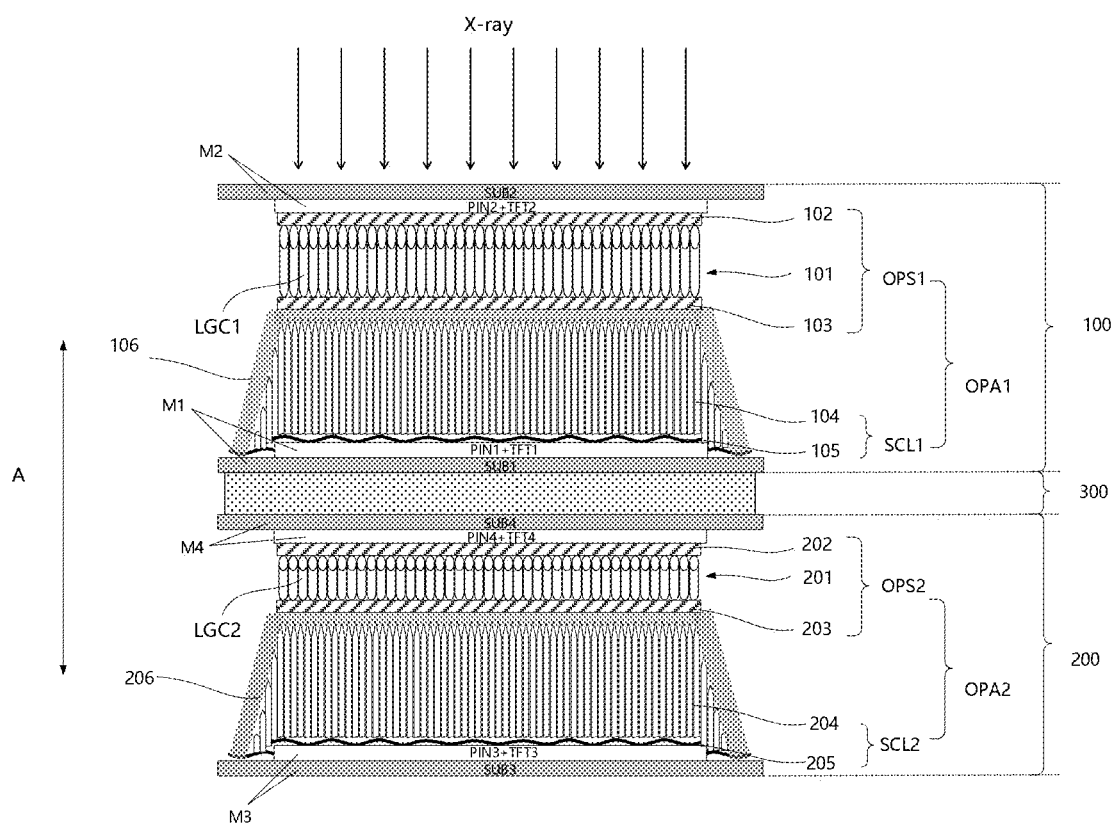
FIG. 14 is still another schematic enlarged sectional view of the flat panel detector according to the embodiments of the present disclosure.

FIG. 14 is still another schematic enlarged sectional view of the flat panel detector according to the embodiments of the present disclosure. For example, as shown in FIG. 14, the first detection unit 100 is consisted of the first image sensor M1, the first optical assembly OPA1 and the second image sensor M2. For example, the first optical assembly OPA1 includes the first scintillator layer SCL1 and the first light guide component OPS1. For example, the first light guide component OPS1 includes the first optical fiber LCG1, the first upper adhesive layer 102 and the first lower adhesive layer 103. In this embodiment, the specific structures of the above components of the first detection unit 100 can be referred to the descriptions in the previous embodiments, and will not be described in detail here.

For example, as shown in FIG. 14, the second detection unit 200 is consisted of the third image sensor M3, the second optical assembly OPA2 and the fourth image sensor M4. In this embodiment, the specific structure and arrangement mode of the third image sensor M3 and the fourth image sensor M4 may refer to the specific description of the first image sensor and the second image sensor in the previous embodiments, which will not be repeated here.

For example, as shown in FIG. 14, the second optical assembly OPA2 includes the second scintillator layer SCL2 and the second light guide component OPS2, and the second light guide component is configured to be stacked with the second scintillator layer SCL2 and configured for guiding the second visible light (including the second downward visible light L3 and the second upward visible light L4). In this embodiment, the specific structure and arrangement mode of the second scintillator layer SCL2 and the second light guide component OPS2 may refer to the specific description of the first scintillator layer and the first light guide component in the previous embodiments, and will not be repeated here. In FIG. 14, the second light guide component is arranged on the upper side of the second scintillator layer SCL2. It can be understood that in other embodiments, the second light guide component is arranged on the lower side of the second scintillator layer SCL2, or the second light guide component is arranged on the upper and lower sides of the second scintillator layer SCL2. That is, according to actual needs, the second light guide component is arranged on one side or both sides of the second scintillator layer, which is not limited by the embodiments of the present disclosure.

In the above embodiments, the second light guide component OPS2 stacked with the second scintillator layer SCL2 is provided in the flat panel detector, and the space distance between the third image sensor M3 and the fourth image sensor M4 is increased by the second light guide component OPS2, which is beneficial to eliminate the electromagnetic interference between the two image sensors and improve the detection quantum efficiency (DQE) of the flat panel detector. Furthermore, in the above embodiments, the second light guide component OPS2 guides the second visible light generated by the second scintillator layer SCL2 to the third image sensor M3 and the fourth image sensor M4, respectively. The second light guide component has a limiting effect on the guided second visible light, which avoids the decrease of the modulation transfer function MTF of the flat panel detector, effectively improves the DQE of the flat panel detector or reduces the usage dosage of X-rays.

For example, as shown in FIG. 14, the second light guide component OPS2 includes a second optical fiber LCG2, which is located on at least one side (the upper side in the figure) of the second scintillator layer SCL1 in the thickness direction of the flat panel detector. In this embodiment, the specific structure and arrangement of the second optical fiber LCG2 may refer to the specific description of the first optical fiber in the previous embodiments, and will not be described here again.

In this embodiment, the second optical fiber LGC1 guides the second upward visible light L4 emitted from the upper surface of the second scintillator layer SCL2 into the fourth image sensor M4 by way of total reflection. In this way, the loss in the transmission process of the second upward visible light L4 is reduced, and the second upward visible light L4 is limited, so that the decrease of MTF is avoided. It can be understood that in the case that the flat panel detector includes two second light guide components, each of which includes the second optical fiber, the second optical fiber is arranged on the upper and lower sides of the second scintillator layer, so that the second downward visible light L3 and the second upward visible light L4 are respectively transmitted to the third image sensor M3 and the fourth image sensor M4 by way of total reflection. In this way, the loss in the transmission process of the second downward visible light L1 and the second upward visible light L2 is reduced, and both the second downward visible light L1 and the second upward visible light L2 is limited, so that the decrease of MTF is further avoided.

For example, as shown in FIG. 14, the second optical fiber LCG2 is located between the second scintillator layer SCL2 and the fourth image sensor M4. For example, the second optical fiber LCG2 has the same structure as the first optical fiber LCG1 shown in FIG. 4. In at least one example, the second optical fiber LCG2 includes a second visible light incident end (not shown in the figure) close to the second scintillator layer SCL2 and a second visible light emergent end (not shown in the figure) far away from the second scintillator layer SCL2, and the second visible light enters the second optical fiber LCG2 through the second visible light incident end and exits the second optical fiber LCG2 through the second visible light emergent end towards the fourth image sensor M4.

For example, as shown in FIG. 14, the second light guide component includes a plurality of second optical fibers LGC2, which are tightly arranged. For example, in the plane of the second scintillator layer SCL2 (the xy plane shown in the figure), the plurality of the second optical fibers LGC2 are arranged in an array, and two adjacent second optical fibers LGC2 are in contact with each other. In this way, the gaps between the second optical fibers are reduced, and the light loss of the visible light in the transmission process is further reduced. In at least one example, the thickness of the second optical fiber LGC2 ranges from 200 microns to 5 millimeters. In at least one example, the thickness of the second optical fiber is regarded as the thickness of the optical fiber layer composed of the second optical fibers. For example, as shown in FIG. 14, the plurality of first optical fibers LGC2 constitute the second optical fiber layer 201, and the thickness of the second optical fiber layer 201 ranges from 200 microns to 5 millimeters.

In at least some embodiments, the second light guide component further includes a second adhesive layer, and the second optical fiber is attached to the second scintillator layer and the fourth image sensor through the second adhesive layer, respectively. For example, as shown in FIG. 14, the second light guide component OPS2 further includes a second upper adhesive layer 202 and a second lower adhesive layer 203. In this embodiment, the specific structure and arrangement of the second adhesive layer may refer to the specific description of the first adhesive layer in the previous embodiments, and will not be repeated here.

For example, as shown in FIG. 14, the thickness of the first scintillator layer SCL1 is greater than or equal to the thickness of the second scintillator layer SCL2. In this way, the second scintillator layer SCL2 allows the flat panel detector to have higher MTF, and the first scintillator layer SCL1 allows the flat panel detector to have higher sensitivity. In at least one example, each of the thickness of the first scintillator layer SCL1 and the thickness of the second scintillator layer SCL2 is between 50 microns and 500 microns, for example between 100 microns and 400 microns. The thickness of the first scintillator layer SCL1 is preferably about 300 microns. The thickness of the second scintillator layer SCL2 is preferably about 200 microns. For example, as shown in FIG. 14, the second scintillator layer SCL2 includes a second columnar crystal scintillator 204 and a second amorphous scintillator 205 located at the bottom of the second columnar crystal scintillator 204. For example, the thickness of the second columnar crystal scintillator 204 is greater than that of the first columnar crystal scintillator 104.

In at least some embodiments, the third image sensor includes a third display region, and the third display region includes a plurality of third wires. The third image sensor further includes a third non-display region surrounding the third display region, and the third non-display region includes a third connection part, in which a third connection wire corresponding to the third wire is arranged, and the third connection wire is electrically connected with the third wire. In this embodiment, the specific structure and arrangement of the third display region, the third wire and the third connection part may refer to the description of the first display region, the first wire and the first connection part in the previous embodiments, and will not be repeated here.

In at least some embodiments, the fourth image sensor includes a fourth display region, and the fourth display region includes a fourth wire. The fourth image sensor further includes a fourth non-display region surrounding the fourth display region, and the fourth non-display region includes a fourth connection part, in which a fourth connection wire corresponding to the fourth wire is provided, and the fourth connection wire is electrically connected with the fourth wire. In this embodiment, the specific structure and arrangement of the fourth display region, the fourth wire and the fourth connection part may refer to the description of the second display region, the second wire and the second connection part in the previous embodiments, and will not be repeated here.

In at least some embodiments, in the thickness direction of the flat panel detector, the third display region and the fourth display region overlap with each other, and the third connection part and the fourth connection part do not overlap with each other. In this way, the signals of the external control circuits (including the driving circuit and the readout circuit) of the third image sensor M3 and the fourth image sensor M4 are prevented from interfering with each other, thus improving the sensitivity and integration of the flat panel detector.

In at least some embodiments, the third wire includes a third gate wire and a third data wire crossing each other; the third connection part includes a third data wire connection part and a third gate wire connection parts, which are located at the fifth edge and the sixth edge of the third display region, respectively, and the fifth edge and the sixth edge are adjacent to each other and connected with each other. In at least some embodiments, the third image sensor M3 further includes a third driving circuit and a third readout circuit. In this embodiment, the specific structure and arrangement of the third gate wire, the third data wire, the third data wire connection part, the third gate wire connection part, the third driving circuit and the third readout circuit may refer to the first gate wire, the first data wire, the first data wire connection part, the first gate wire connection part, the first driving circuit and the first readout circuit in the previous embodiments, and will not be described here again. The specific structure and arrangement of the fifth edge and the sixth edge of the third display region may refer to the previous description of the first edge and the second edge of the first display region, which will not be repeated here.

In at least some embodiments, the fourth wire includes a fourth gate wire and a fourth data wire crossing with each other; the fourth connection part includes a fourth gate wire connection part and a fourth data wire connection part, the fourth gate wire connection part and the fourth data wire connection part are respectively located at the seventh edge and the eighth edge of the fourth display region, and the seventh edge and the eighth edge are adjacent to each other and connected with each other. The fourth image sensor M4 further includes a fourth driving circuit and a fourth readout circuit. In this embodiment, the specific structure and arrangement of the fourth gate wire, the fourth data wire, the fourth data wire connection part, the fourth gate wire connection part, the fourth driving circuit and the fourth readout circuit may refer to the second gate wire, the second data wire, the second data wire connection part, the second gate wire connection part, the second driving circuit and the second readout circuit in the previous embodiments, and will not be repeated here. The specific structure and arrangement of the seventh edge and the eighth edge of the fourth display region may refer to the previous description of the third edge and the fourth edge of the second display region, which will not be repeated here.

By the arrangement of the connection part and the wire in the above embodiment, the fourth connection wire, the fourth connection part, the fourth driving circuit and the fourth reading circuit of the fourth image sensor M4 are avoided from overlapping with the second connection wire, the second connection part, the second driving circuit and the second reading circuit of the second image sensor, thus avoiding the interference of signals between the two image sensors.

For example, as shown in FIG. 14, the flat panel detector further includes the first encapsulation layer 106 that seals at least the first image sensor M1 and the first scintillator layer SCL1. In this way, water vapor and impurities are prevented from entering the first image sensor M1 and the first scintillator layer SCL1. In this embodiment, the specific structure and arrangement mode of the first encapsulation layer 106 may refer to the description of the previous embodiments, and will not be repeated here.

For example, as shown in FIG. 14, the flat panel detector further includes a second encapsulation layer 206 that seals at least the third image sensor M3 and the second scintillator layer SCL2. In this way, water vapor and impurities are prevented from entering the third image sensor M3 and the second scintillator layer SCL2. In this embodiment, the specific structure and arrangement mode of the second encapsulation layer 206 may refer to the description of the first encapsulation layer 106, which will not be repeated here. It can be understood that the first encapsulation layer 106 and the second encapsulation layer 206 are different from each other in structure. For example, the first encapsulation layer 106 seals the first image sensor M1 and the first scintillator layer SCL1, and the second encapsulation layer 206 seals the third image sensor M3, the second light guide component OPS2 and the second scintillator layer SCL2. In at least one example, in the case that the first encapsulation layer 106 and the second encapsulation layer 206 have the same structure, the manufacturing process can be simplified, which therefore is preferable.

As shown in FIGS. 13 and 14, the flat panel detector further includes a shielding assembly 300, which is located between the first detection unit 100 and the second detection unit 200. Further, the shielding assembly 300 is located between the first image sensor M1 and the fourth image sensor M4, and is configured for shielding ultraviolet rays and electromagnetic waves with wavelengths longer than ultraviolet rays. In this way, electromagnetic waves (such as visible light) in the above wavelength range are prevented from entering the second detection unit 200, and interference on the second detection unit 200 is avoided.

Figure 15:
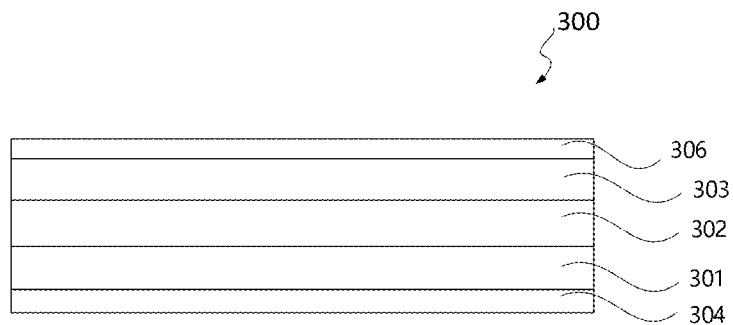
FIG. 15 is a schematic sectional view of a shielding assembly of the flat panel detector according to the embodiments of the present disclosure.

In at least some embodiments, the shielding assembly includes a shielding layer having a single-layer structure or a multi-layer structure. For example, the multi-layer structure includes two or more layers. FIG. 15 is a schematic sectional view of the shielding assembly of the flat panel detector according to the embodiments of the present disclosure. For example, as shown in FIG. 15, the shielding assembly includes a first shielding layer 301, a second shielding layer 302 and a third shielding layer 303. For example, the first shielding layer 301 shields electromagnetic waves in the first wavelength range, the second shielding layer 302 shields electromagnetic waves in the second wavelength range, the third shielding layer 303 shields electromagnetic waves in the third wavelength range, and the first wavelength range, the second wavelength range and the third wavelength range are different from each other. In at least one example, the first wavelength range corresponds to the ultraviolet wavelength range, for example, 10 nm to 100 nm. In at least one example, the second wavelength range corresponds to the visible light wavelength range, for example, 100 nm to 760 nm. In at least one example, the third wavelength range corresponds to the infrared wavelength range, for example, greater than 760 nm.

In at least some embodiments, the shielding layer has a single-layer structure, which is configured to absorb long-wavelength X-rays (referred to as soft rays for short), so that short-wavelength X-rays (referred to as hard rays for short) is transmitted. In this way, the first detection unit is configured to detect X-rays with a large wavelength range (i.e. soft rays and hard rays), and the second detection unit is configured to detect X-rays with a small wavelength range (i.e. only hard rays).

In at least some embodiments, the shielding layer comprises a metal material, and the thickness of the shielding layer ranges from 200 microns to 5 millimeters. In at least one example, the thicknesses of the first shielding layer 301, the second shielding layer 302 and the third shielding layer 303 may be the same to or different from each other.

In at least some embodiments, the shielding assembly further includes a third adhesive layer, and the shielding layer is attached to the first image sensor and the fourth image sensor respectively through the third adhesive layer. For example, as shown in FIGS. 14 and 15, the shielding assembly further includes a third adhesive layer for attaching the shielding layer to the first image sensor M1 and the fourth image sensor M4. For example, the adhesive layers include a first adhesive layer 306 and a second adhesive layer 304. The first adhesive layer 306 is located between the third shielding layer 303 and the first image sensor M1. The second adhesive layer 304 is located between the first shielding layer 301 and the fourth image sensor M4.

In the embodiments of the disclosure, both the first optical fiber and the second optical fiber include a core and a cladding layer covering the core. For example, the core is made of a transparent material such as glass, quartz or plastic. For example, the cladding layer comprises a light-transmitting material with low refractive index. In at least one example, the diameters of the first optical fiber and the second optical fiber are between several microns and tens of microns. In the embodiments of the disclosure, in the case that light rays (such as X-rays) are incident from one end of the optical fiber, the incident angle of those light rays with small incident angle at the core-cladding layer interface of the optical fiber is greater than the critical angle of total reflection, so that the light rays are continuously totally reflected in the optical fiber, and the light rays are transmitted from one end of the optical fiber to the other end of the optical fiber with the lowest loss.

In the embodiments of the disclosure, the first substrate SUB1, the second substrate SUB2, the third substrate SUB3 and the fourth substrate SUB4 adopt rigid or flexible substrates, the rigid substrate for example is glass, and the flexible substrate for example is polyimide (PI) substrate. The absorption of X-rays by the flexible substrate is far less than that by glass substrate. Using flexible substrate can improve the signal-to-noise ratio of the products. In at least one example, in the case that at least one of the above substrates is a flexible substrate, the overall weight of the flat panel detector is reduced, and the attenuation of X-rays is reduced, which therefore is preferable.

Figure 16:
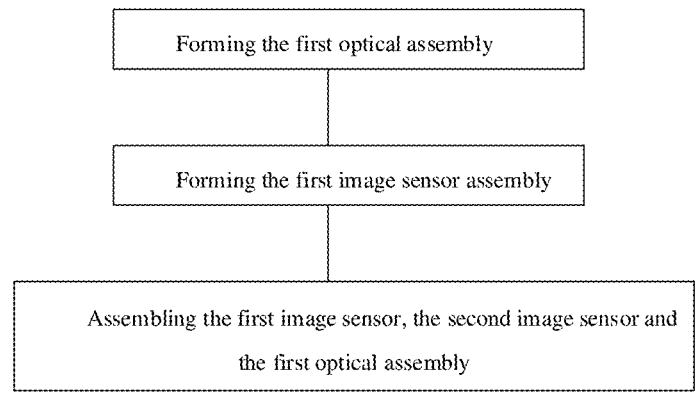
FIG. 16 is a flow chart of a manufacturing method of the flat panel detector according to the embodiments of the disclosure.

FIG. 16 is a flow chart of a manufacturing method of the flat panel detector according to the embodiments of the disclosure. As shown in FIG. 16, the embodiments of the present disclosure further provide a manufacturing method of the flat panel detector, which includes:

Forming a first optical assembly, in which the first optical assembly has a first side and a second side opposite to the first side in the thickness direction of the flat panel detector, and the first optical assembly comprises a first scintillator layer for converting at least part of X-rays into a first visible light; and a first light guide component configured to be stacked with the first scintillator layer for guiding the first visible light;

Forming a first image sensor assembly, in which the first image sensor assembly is configured to be stacked with the first optical assembly and configured for receiving the first visible light, and the first image sensor assembly includes a first image sensor and a second image sensor; and Assembling the first image sensor, the second image sensor and the first optical assembly so that the first image sensor and the second image sensor are located on the first side of the first optical assembly and the second side of the first optical assembly, respectively, to form a first detection unit.

In the manufacturing method of the above embodiments, by forming the second image sensor on the upper side of the first scintillator layer, part of the first visible light emitted from the upper surface of the first scintillator layer reaches the second image sensor to image, thus reducing the loss caused by the first visible light propagating in the first scintillator layer. Further, in the manufacturing method of the above embodiments, the first light guide component stacked with the first scintillator layer is formed in the flat panel detector, and the space distance between the first image sensor and the second image sensor is increased by the first light guide component, which is beneficial to eliminate the electromagnetic interference between the two image sensors and improve the DQE of the flat panel detector. Furthermore, in the manufacturing method of the above embodiments, the first light guide component guides the first visible light generated by the first scintillator layer to the first image sensor assembly; because the first light guide component has a limiting effect on the guided first visible light, the MTF of the flat panel detector is prevented from decreasing, and the DQE of the flat panel detector is effectively improved or the usage dosage of X-rays is reduced.

In at least some embodiments, by using the above manufacturing method of the flat panel detector, the method of manufacturing the flat panel detector of FIG. 2A or FIG. 13 includes:

Forming the first optical assembly OPA1, in which the first optical assembly OPA1 has the first side 11 and the second side 12 opposite to the first side 11 in the thickness direction A of the flat panel detector, and the first optical assembly OPA1 includes the first scintillator layer SCL1 for converting at least part of X-rays into the first visible light (including the first downward visible light L1 and the first upward visible light L2); and the first light guide component configured to be stacked with the first scintillator layer SCL1 for guiding the first visible light;

Forming the first image sensor assembly, in which the first image sensor assembly is configured to be stacked with the first optical assembly OPA1 and configured for receiving the first visible light, the first image sensor assembly including the first image sensor M1 and the second image sensor M2; and Assembling the first image sensor M1, the second image sensor M1 and the first optical assembly OPA1 so that the first image sensor M1 and the second image sensor M1 are located on the first side 11 and the second side 12 of the first optical assembly OPA1, respectively, to form the first detection unit 100.

Figure 17:
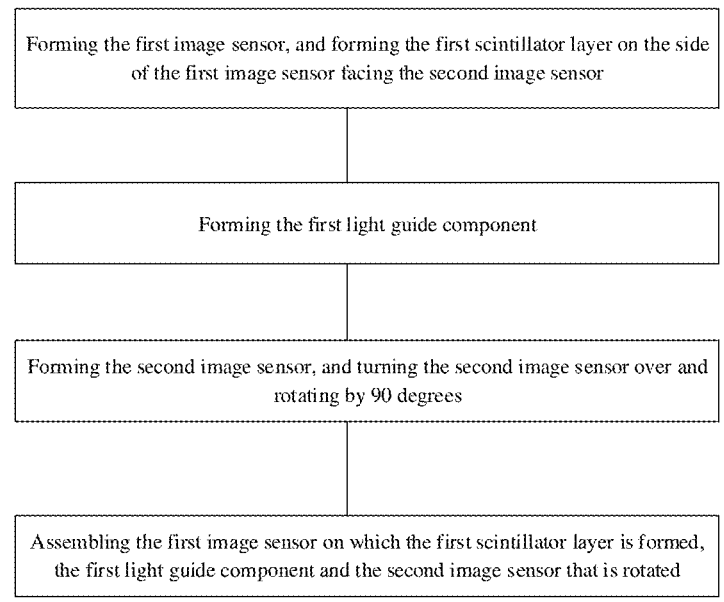
FIG. 17 is another flow chart of the manufacturing method of the flat panel detector according to the embodiments of the present disclosure.
Figures 18A, 18B, 18C, 18D, 18E, 18F, 19:
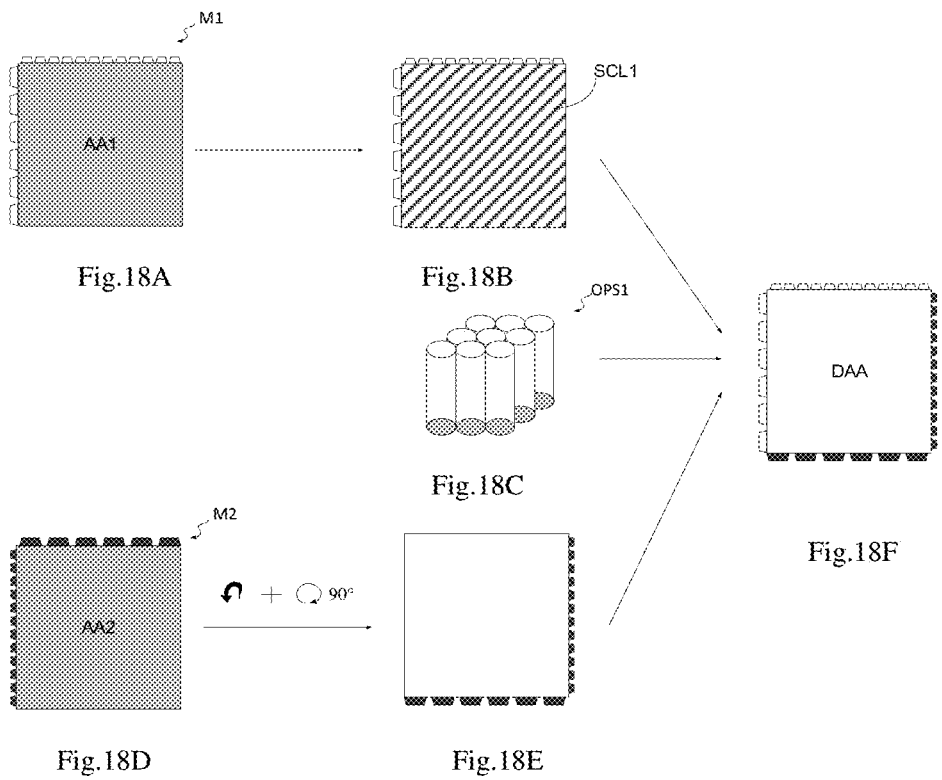
FIGS. 18A to 18F are schematic views of respective steps of the manufacturing method of the flat panel detector according to the embodiments of the present disclosure.
FIG. 19 is still another flow chart of the manufacturing method of the flat panel detector according to the embodiments of the present disclosure.

FIG. 17 is another flow chart of the manufacturing method of the flat panel detector according to the embodiments of the present disclosure. FIGS. 18A to 18F are schematic views of respective steps of the manufacturing method of the flat panel detector according to the embodiments of the present disclosure. For example, as shown in FIG. 17, the manufacturing method of the flat panel detector according to the embodiments of the present disclosure includes:

Forming the first image sensor M1, and forming the first scintillator layer SCL1 on the side of the first image sensor M1 facing the second image sensor M2, as shown in FIGS. 18A and 18B;

Forming the first light guide component OPS1 as shown in FIG. 18C;

Forming the second image sensor M2, and turning the second image sensor M2 over and rotating by 90 degrees, as shown in FIGS. 18D and 18E; and Assembling the first image sensor M1 on which the first scintillator layer SCL1 is formed, the first light guide component OPS1 and the second image sensor M2 that is rotated.

For example, forming the first scintillator layer SCL1 includes forming the first scintillator layer SCL1 on the first image sensor M1 by thermal evaporation.

FIG. 19 is still another flow chart of the manufacturing method of the flat panel detector according to the embodiments of the present disclosure. For example, as shown in FIG. 19, the method of manufacturing the flat panel detector of FIG. 2A according to the embodiments of the present disclosure includes:

Forming the first image sensor M1, and forming the first scintillator layer SCL1 on the side of the first image sensor M1 facing the second image sensor M2;

Attaching the first light guide component OPS1 to the first scintillator layer SCL1;

Directly forming the second image sensor M2 on the first light guide component OPS1.

In at least some embodiments, the manufacturing method further includes packaging the first scintillator layer SCL1, the first light guide component OPS1 and the first image sensor M1. In at least one example, the packaging is performed by using the light-transmitting material.

In the manufacturing method of at least some embodiments, assembling the first image sensor M1, the second image sensor M2 and the first optical assembly OPA1 includes: adhering them to each other with an adhesive or assembling them with each other with a vacuum adsorption method. In at least one example, the first image sensor M1, the second image sensor M2 and the first optical assembly OPA1 are assembled together by a vacuum adsorption method, so that the use of adhesive is omitted, thereby reducing the interference of adhesive to light during the transmission of light.

In the manufacturing method of at least some embodiments, in order to improve the alignment accuracy of the first image sensor M1 and the second image sensor M2, a first alignment mark is provided in the first non-display region NA1 of the first image sensor M1 and a second alignment mark is provided in the second non-display region NA2 of the second image sensor M2, so that the first alignment mark is aligned with the second alignment mark during assembly, and a better assembly effect can be achieved. For example, a charge coupled device (CCD) is used for alignment, and the accuracy reaches ±50 μm.

For example, as shown in FIG. 13, the above manufacturing method further includes:

Forming a second optical assembly OPA2, in which the second optical assembly OPA2 is located on the side of the first image sensor M1 far away from the first optical assembly OPA1 and is configured to be stacked with the first optical assembly OPA1 and the first image sensor assembly, the second optical assembly OPA2 has a third side 112 and a fourth side 111 opposite to the third side 112 in the thickness direction A of the flat panel detector, and the fourth side 111 is closer to the first image sensor M1 than the third side 112, and the second optical assembly OPA2 includes a second scintillator layer SCL2 for converting at least another part of X-rays into a second visible light (including a second downward visible light L3 and a second upward visible light L4); and Forming a second image sensor assembly, in which the second image sensor assembly is configured to be stacked with the second optical assembly OPA2 and is configured for receiving the second visible light, and the second image sensor assembly includes a third image sensor M3 and a fourth image sensor M4;

Assembling the third image sensor M3, the fourth image sensor M4 and the second optical assembly OPA2 so that the third image sensor M3 is located on the third side 112 of the second optical assembly OPA2 and the fourth image sensor M4 is located on the fourth side 111 of the second optical assembly OPA2 to form a second detection unit 200;

Assembling the second detection unit 200 with the first detection unit 100.

For example, as shown in FIG. 13, forming the second optical assembly OPA2 further comprises forming a second light guide component OPS2, in which the second light guide component OPS2 is configured to be stacked with the second scintillator layer SCL2 and configured for guiding the second visible light.

In at least some embodiments, the manufacturing method of the second detection unit 200 may refer to the manufacturing method of the first detection unit 100 in the previous embodiments.

For example, referring to FIGS. 17 and 19, the manufacturing method includes:

Forming the third image sensor M3, and forming the second scintillator layer SCL2 on the side of the third image sensor M3 facing the fourth image sensor M4;

Forming the second light guide component OPS2;

Forming the fourth image sensor M4, and turning the fourth image sensor M4 over and rotating by 90 degrees; and Assembling the third image sensor M3 on which the second scintillator layer SCL2 is formed, the second light guide component OPS2 and the fourth image sensor M4 that is rotated.

For example, referring to FIG. 14, the manufacturing method includes:

Forming the third image sensor M3, and forming the second scintillator layer SCL2 on the side of the third image sensor M3 facing the fourth image sensor M4;

Attaching the second light guide component OPS2 to the second scintillator layer SCL2;

Directly forming the fourth image sensor M4 on the second light guide component OPS2.

In at least some embodiments, the manufacturing method further includes packaging the second scintillator layer SCL2, the second light guide component OPS2 and the third image sensor M3. For specific packaging methods, please refer to the previous detailed description of packaging the first scintillator layer SCL1, the first light guide component OPS1 and the first image sensor M1, which will not be repeated here.

In the manufacturing method of at least some embodiments, assembling the third image sensor M3, the fourth image sensor M4 and the second optical assembly includes adhering them to each other with an adhesive or assembling them with each other with a vacuum adsorption method. The detailed description of the previous embodiments for the specific assembly mode may be refer to, which will not be described here again.

In the manufacturing method of at least some embodiments, a third alignment mark is provided in the third non-display region of the third image sensor M3, and a fourth alignment mark is provided in the fourth non-display region of the fourth image sensor M4, so that the third alignment mark is aligned with the fourth alignment mark during assembly, and a better assembly effect can be achieved.

In the manufacturing method of at least some embodiments, during assembling the first detection unit and the second detection unit, the above-mentioned alignment marks are used to improve the alignment accuracy of the two detection units.

For example, as shown in FIG. 13, the above manufacturing method further includes: forming a shielding assembly 300 located between the first image sensor M1 and the fourth image sensor M4 for shielding ultraviolet rays and electromagnetic waves longer than ultraviolet rays.

The flat panel detector and the manufacturing method thereof according to the embodiments of the disclosure have the following advantages and technical effects:

1) By arranging the second image sensor on the upper side of the first scintillator layer, part of the first visible light emitted from the upper surface of the first scintillator layer reaches the second image sensor to image, thus reducing the loss caused by the propagation of the first visible light in the scintillator layer.

2) By arranging the first light guide component stacked with the first scintillator layer in the flat panel detector, the space distance between the first image sensor and the second image sensor is increased by using the first light guide component, which is beneficial to eliminate the electromagnetic interference between the two image sensors and improve the DQE of the flat panel detector.

3) The first light guide component guides the first visible light generated by the first scintillator layer to the first image sensor and the second image sensor respectively. Because the first light guide component has a limiting effect on the guided first visible light, the decrease of the modulation transfer function (MTF) of the flat panel detector is avoided, the DQE of the flat panel detector is effectively improved or the usage dosage of X-rays is reduced.

4) The flat panel detector with dual detection units collects more X-rays, obtains more complete image information, and further improves MTF and sensitivity of the flat panel detector, so as to obtain better image quality.

5) The shielding assembly between the two detection units is configured to shield ultraviolet rays and electromagnetic waves with wavelengths longer than ultraviolet rays. In this way, it is possible to avoid the interference of electromagnetic waves in the above wavelength range on the second detection unit.

The foregoing descriptions are merely exemplary implementations of the present disclosure, and are not used to limit the protection scope of the present disclosure, which is determined by the appended claims.

What is claimed is:

1. A flat panel detector comprising:
   a first optical assembly, having a first side and a second side opposite to the first side in a thickness direction of the flat panel detector, and comprising:
   a first scintillator layer configured for converting at least part of rays into a first visible light; and
   a first light guide component stacked with the first scintillator layer and configured for guiding the first visible light;
   a first image sensor assembly stacked with the first optical assembly, configured for receiving the first visible light, and comprising:
   a first image sensor located at the first side of the first optical assembly; and
   a second image sensor located at the second side of the first optical assembly, wherein:
   the first image sensor comprises:
   a first display region comprising a plurality of first wires;
   a first non-display region surrounding the first display region, wherein the first non-display region comprises a first connection part, a first connection wire corresponding to the first wire is provided in the first connection part, and the first connection wire is electrically connected with the first wire;
   the second image sensor comprises:
   a second display region comprising a second wire;
   a second non-display region surrounding the second display region, wherein the second non-display region comprises a second connection part, a second connection wire corresponding to a second wire is provided in the second connection part, and the second connection wire is electrically connected with the second wire;
   in the thickness direction of the flat panel detector, the first display region and the second display region overlap with each other, and the first connection part and the second connection part do not overlap with each other.

2. The flat panel detector according to claim 1, wherein the first light guide component comprises a first optical fiber, and the first optical fiber is located at least on one side of the first scintillator layer in the thickness direction of the flat panel detector.

3. The flat panel detector according to claim 2, wherein:
   the first optical fiber is located between the first scintillator layer and the second image sensor;
   the first optical fiber comprises a first visible light incident end close to the first scintillator layer and a first visible light emergent end far away from the first scintillator layer;
   the first visible light enters the first optical fiber through the first visible light incident end and exits the first optical fiber through the first visible light emergent end towards the second image sensor.

4. The flat panel detector according to claim 2, wherein:
   the first light guide component further comprises a first adhesive layer, and the first optical fiber is respectively attached to the first scintillator layer and the second image sensor through the first adhesive layer.

5. The flat panel detector as claimed in claim 1, wherein:
   the first wire comprises a first gate wire and a first data wire crossing each other, the first connection part comprises a first gate wire connection part and a first data wire connection part, the first gate wire connection part and the first data wire connection part are located at a first edge and a second edge of the first display region, respectively, and the first edge and the second edge of the first display region are adjacent to each other and connected with each other;

the second wire comprises a second gate wire and a second data wire crossing each other, the second connection part comprises a second gate wire connection part and a second data wire connection part, the second gate wire connection part and the second data wire connection part are located at a third edge and a fourth edge of the second display region, respectively, and the third edge and the fourth edge of the second display region are adjacent to and connected with each other.

6. The flat panel detector according to claim 1, further comprising:
a second optical assembly, located at a side of the first image sensor far away from the first optical assembly, stacked with the first optical assembly and the first image sensor assembly and comprising a second scintillator layer configured for converting at least another part of the rays into a second visible light;
a second image sensor assembly, stacked with the second optical assembly, configured for receiving the second visible light, and comprising a third image sensor located on a side of the second optical assembly far away from the first optical assembly.

7. The flat panel detector of claim 6, wherein:
the second image sensor assembly further comprises a fourth image sensor;
the second optical assembly has a third side and a fourth side opposite to the third side in the thickness direction of the flat panel detector, the fourth side is closer to the first image sensor than the third side, the third image sensor is located on the third side of the second optical assembly, and the fourth image sensor is located on the fourth side of the second optical assembly.

8. The flat panel detector of claim 7, wherein:
the second optical assembly further comprises a second light guide component, the second light guide component is stacked with the second scintillator layer and is configured for guiding the second visible light to the second image sensor assembly.

9. The flat panel detector according to claim 8, wherein:
the second light guide component comprises a second optical fiber, and the second optical fiber is located at least on one side of the second scintillator layer in the thickness direction of the flat panel detector.

10. The flat panel detector of claim 9, wherein:
the second optical fiber is located between the second scintillator layer and the fourth image sensor, the second optical fiber comprises a second visible light incident end close to the second scintillator layer and a second visible light emergent end far away from the second scintillator layer, and the second visible light enters the second optical fiber through the second visible light incident end and exits the second optical fiber through the second visible light emergent end towards the fourth image sensor.

11. The flat panel detector according to claim 10, wherein:
the first light guide component comprises a plurality of first optical fibers, and the second light guide component comprises a plurality of second optical fibers;
the plurality of first optical fibers are tightly arranged, a comprised angle between a length direction of each of the plurality of first optical fibers and a plane where the first scintillator layer is located is greater than or equal to 45 degrees and less than or equal to 90 degrees, and a thickness of the first optical fiber ranges from 200 microns to 5 millimeters;
the plurality of second optical fibers are tightly arranged, an included angle between a length direction of each of the plurality of second optical fibers and a plane where the second scintillator layer is located is greater than or equal to 45 degrees and less than or equal to 90 degrees, and a thickness of the second optical fiber ranges from 200 microns to 5 millimeters.

12. The flat panel detector according to claim 7, wherein a thickness of the first scintillator layer is greater than or equal to a thickness of the second scintillator layer.

13. The flat panel detector according to claim 7, further comprising a shielding assembly located between the first image sensor and the fourth image sensor and configured for shielding ultraviolet rays and electromagnetic waves with a wavelength longer than the ultraviolet rays.

14. The flat panel detector of claim 13, wherein the shielding assembly comprises a shielding layer having a single-layer structure or a multi-layer structure, the shielding layer comprises a metal material, and a thickness of the shielding layer ranges from 200 microns to 5 millimeters.

15. The flat panel detector according to claim 14, wherein the shielding assembly further comprises a third adhesive layer, and the shielding layer is respectively attached to the first image sensor and the fourth image sensor by the third adhesive layer.

16. The flat panel detector according to claim 7, wherein:
the third image sensor comprises:
a third display region comprising a plurality of third wires;
a third non-display region surrounding the third display region, wherein the third non-display region comprises a third connection part, a third connection wire corresponding to the third wire is provided in the third connection part, and the third connection wire is electrically connected with the third wire;
the fourth image sensor comprises:
a fourth display region comprising a fourth wire;
a fourth non-display region surrounding the fourth display region, wherein the fourth non-display region comprises a fourth connection part, a fourth connection wire corresponding to the fourth wire is provided in the fourth connection part, and the fourth connection wire is electrically connected with the fourth wire;
in the thickness direction of the flat panel detector, the third display region and the fourth display region overlap with each other, and the third connection part and the fourth connection part do not overlap with each other.

17. The flat panel detector as claimed in claim 16, wherein:
the third wire comprises a third gate wire and a third data wire crossing each other, the third connection part comprises a third data wire connection part and a third gate wire connection part, the third data wire connection part and the third gate wire connection part are respectively located at a fifth edge and a sixth edge of the third display region, and the fifth edge and the sixth edge of the third display region are adjacent to each other and connected with each other;
the fourth wire comprises a fourth gate wire and a fourth data wire crossing each other, the fourth connection part comprises a fourth gate wire connection part and a fourth data wire connection part, the fourth gate wire connection part and the fourth data wire connection part are respectively located at a seventh edge and a eighth edge of the fourth display region, and the seventh edge and the eighth edge of the fourth display region are adjacent to each other and connected with each other.

18. A method of manufacturing a flat panel detector, comprising:

forming a first optical assembly having a first side and a second side opposite to the first side in the thickness direction of the flat panel detector, wherein the first optical assembly comprises: a first scintillator layer configured for converting at least part of rays into a first visible light; and a first light guide component stacked with the first scintillator layer and configured for guiding the first visible light;

forming a first image sensor assembly stacked with the first optical assembly and configured for receiving the first visible light, wherein the first image sensor assembly comprising a first image sensor and a second image sensor; and assembling the first image sensor, the second image sensor and the first optical assembly so that the first image sensor and the second image sensor are respectively located on the first side and the second side of the first optical assembly, so as to form a first detection unit, wherein the manufacturing method comprises:

forming the first image sensor, and forming the first scintillator layer on a side of the first image sensor facing the second image sensor;

forming the first light guide component;

forming the second image sensor, and turning the second image sensor over and rotating by 90 degrees; and assembling the first image sensor on which the first scintillator layer is formed, the first light guide component and the second image sensor that is rotated.

* * * * *